United States Patent
Ozeki et al.

(10) Patent No.: US 9,724,318 B2
(45) Date of Patent: Aug. 8, 2017

(54) COMPOSITIONS FOR IMPROVING MENTAL CONCENTRATION

(75) Inventors: Makoto Ozeki, Yokkaichi (JP); Tomoko Kumagai, Yokkaichi (JP); Tsutomu Okubo, Yokkaichi (JP); Lekh Raj Juneja, Yokkaichi (JP)

(73) Assignee: TAIYO KAGAKU CO., LTD., Yokkaichi-Shi (JP)

(*) Notice: Subject to any disclaimer, the term of this patent is extended or adjusted under 35 U.S.C. 154(b) by 0 days.

(21) Appl. No.: 10/311,972

(22) PCT Filed: Sep. 7, 2001

(86) PCT No.: PCT/JP01/07764
§ 371 (c)(1),
(2), (4) Date: Feb. 11, 2003

(87) PCT Pub. No.: WO02/089786
PCT Pub. Date: Nov. 14, 2002

(65) Prior Publication Data
US 2005/0020627 A1    Jan. 27, 2005

(30) Foreign Application Priority Data

Apr. 24, 2001 (JP) .................. 2001-126266
Jun. 11, 2001 (JP) .................. 2001-176134

(51) Int. Cl.
| | | |
|---|---|---|
| A61K 31/132 | (2006.01) | |
| A61K 31/133 | (2006.01) | |
| A61K 31/16 | (2006.01) | |
| A61K 31/195 | (2006.01) | |
| A61K 31/198 | (2006.01) | |

(52) U.S. Cl.
CPC .......... *A61K 31/198* (2013.01); *A61K 31/132* (2013.01); *A61K 31/133* (2013.01); *A61K 31/16* (2013.01); *A61K 31/195* (2013.01)

(58) Field of Classification Search
CPC .... A61K 31/19; A61K 31/195; A61K 31/197; A61K 31/198
USPC ................................ 514/626, 563
See application file for complete search history.

(56) References Cited

U.S. PATENT DOCUMENTS

| | | | |
|---|---|---|---|
| 4,871,550 A * | 10/1989 | Millman | ........... 424/601 |
| 5,731,349 A | 3/1998 | Komissarova et al. | |
| 5,736,575 A * | 4/1998 | Kakuda et al. | ........... 514/563 |
| 5,780,086 A | 7/1998 | Kirksey et al. | |
| 6,271,259 B1 | 8/2001 | Kakuda et al. | |
| 2005/0020627 A1 | 1/2005 | Ozeki et al. | |

FOREIGN PATENT DOCUMENTS

| | | | |
|---|---|---|---|
| CN | 1370468 A | | 9/2002 |
| EP | 1 057 483 A1 | | 12/2000 |
| JP | 08073350 | * | 3/1996 |
| JP | 9-012454 A | | 1/1997 |
| JP | 9-040568 A | | 2/1997 |
| JP | 9-173017 A | | 7/1997 |
| JP | 9-249556 A | | 9/1997 |
| JP | 11-239465 A | | 9/1999 |
| JP | 2000-026304 A | | 1/2000 |
| JP | 2002-322053 A | | 11/2002 |

OTHER PUBLICATIONS

Tsunoda et al. 125Ca:19092, 1996.*
J.J. Sports Sci., vol. 5, No. 3, (1986), pp. 186-191.
Shokuhin to Kaihatsu, vol. 34, No. 10, (1999), pp. 4-8.
Kagaku, vol. 55, No. 6, (2000), pp. 19-25.
Mason, "200 mg of Zen: L-Theanine Boosts Alpha Waves, Promotes Alert Relaxation", vol. 7, No. 2, 2001, pp. 91-95, XP009059302.
Juneja, et al.., "L-Theanine—A Unique Amino Acid of Green Tea and Its Relaxation Effect in Humans", Trends in Food Science and Technology, Elsevier Science Publishers, GB, vol. 10, No. 12, 1999, pp. 199-204, XP002959796.
Office Action in Japanese Application No. 2001-126266 mailed Jun. 13, 2011.
Office Action in Japanese Application No. 2001-176134 mailed Jun. 13, 2011.
Shinagawa et al., "Shu-chu Ryoku to Nouha (Concentration and EEG)," Rinsho Nouha (Clinical Brain Wave), 1992, vol. 34, No. 3.
Chu et al., "A unique Amino Acid of Green Tea, L-Theanine, and Its Relaxation Effect in Humans," Fragrance Journal, Apr. 2000, vol. 28, No. 4, pp. 74-80 and 111.
Japanese Office Action dated Dec. 16, 2011 for Japanese Application No. 2001-126266.
Japanese Office Action dated Dec. 16, 2011 for Japanese Application No. 2001-176134.
Okubo et al., "Properties of L-Theanine and Utilization for Foods," Japan Food Science, vol. 40, No. 1, Jan. 2001, pp. 33-36 and 96.
Shiga, "Research and Application of Alpha Brain Wave in Creativity," Research Laboratory of Brain Function, Institute of Electronics, Information and Communication Engineers Technical Report, vol. 91, No. 360, Nov. 30, 1991, 7 pages (includes pp. 49-54 and 1 page).
Tokunaga, "Evaluation Scales for Athletes' Psychological Competitive Ability: Development and Systematization of the Scales," Journal of Health Science, vol. 23, Mar. 2001, pp. 91-102.

* cited by examiner

*Primary Examiner* — Yong Chong
(74) *Attorney, Agent, or Firm* — Birch, Stewart, Kolasch & Birch, LLP

(57) ABSTRACT

The present invention provides a composition for improving mind-concentration, characterized in that the composition comprises theanine; and a method of improving mind-concentration comprising administering theanine to an individual.

8 Claims, 18 Drawing Sheets

EXTENT OF CONCENTRATION

THEANINE-FORMULATED CANDY          CONTROL CANDY

FIG.10

| Before Trial Shots | (eye-closed) | 1 min. |
| Trial Shots | (3 shots) | 5 min. |
| After Trial Shots | (eye-closed) | 1 min. |

↓

Break 30 seconds

↓

| Before Scoring Shots | (eye-closed) | 1 min. |
| Scoring Shots | (3 shots) | 5 min. |
| After Scoring Shots | (eye-closed) | 1 min. |

↓

Termination

COMPOSITIONS FOR IMPROVING MENTAL CONCENTRATION

This application is the national phase under 35 U.S.C. §371 of PCT International Application No. PCT/JP01/07764 which has an International filing date of Sep. 7, 2001, which designated the United States of America.

TECHNICAL FIELD

The present invention relates to a composition for improving mind-concentration, and a method of improving mind-concentration.

BACKGROUND ART

The roles played by the mental functions are very important during working, learning or the like. In order to make the most appropriate movement or judgment under the conditions that environments, physical conditions and state of mind vary, it is required to concentrate, thereby instantaneously selecting and deciding the object, and taking actions. Also, in order to maintain the working efficiently, the work must be continued with the mind concentrated. However, in either case, lowering of the working efficiency and judgment is unavoidable due to such reasons as fatigue, continuous working, passage of time, boredom, added age, physical disorders, emotional disorders, tension, surrounding factors such as vibration and noise, lack of motivation, demanding attention, compromise and dependence.

So far, there has been known to take glucose in order to maintain the concentration during working, learning or the like. However, the intake of glucose merely temporarily elevates the blood sugar level and its maintenance is low. Also, there have been known those drugs for enhancing mind-concentration during physical exercise, such as a stimulant including caffeine and cocaine hydrochloride, and a β-blocking agent such as Atenolol. However, these drugs have adverse actions, so that their uses have been prohibited by the International Olympic Committee, Medical Bureau. Also, creatinine preparation has been used, but there has been reported that the effect by the creatinine preparation is not remarkable.

Also, not only acquiring each technique but also exhibiting the technique during a competition in an appropriate situation at a proper timing should be required in order that an athlete shows an excellent performance during physical exercise. Therefore, in addition to the physical exercise abilities, an athlete is further required to be excellent in an ability to concentrate the mind, which is a so-called "concentration ability," without being distracted to other matters during a competition as well as information processing abilities such as anticipation and judgment.

Conventionally, there have been studied various methods for mental training which are purposed for being able to control oneself to a mental state optimum for showing excellent performance, and the methods have been employed in an actual situation. For instance, studies and developments of mind-controlling method and psychological training method have been carried out, and a method for "prevention from becoming nervous (agari)," a method for maintaining a usual state, a method for improving a usual state at least a little, and a method for "enhancing concentration ability" have been carried out. Also, there has been introduced a study using bio-feedback.

The term "bio-feedback" is defined as "an operation of converting person's changes in neural and physiological reactions (for instance, skin temperature, myogenic potential, brain waves, heart beat, and the like) to external information, and transmitting the information to the person."

Generally, it has been known that human shows the best performance when human reaches its optimum vigilance level. The term "vigilance" as referred to herein is an inner state characterized by latent excitement, tension, anxiety and the like. When the vigilance level is elevated, the central nervous system such as decision-making actively functions, so that the accuracy of the reaction and the like increases, namely, the performance is improved. However, when the vigilance level becomes too high, attentiveness is hard to be concentrated, mistakes are made in decision-making, and the limbs become stiff because of overstraining, whereby the performance is lowered.

Therefore, there has been carried out training which brings the level of vigilance to an optimal level by bio-feedback in order that more excellent performance is exhibited. However, the training necessitates many repetitions of lesson, thereby making it time-consuming. Also, there is a large difference between individuals.

On the other hand, there has been also known a method for improving sports performance by supplementing nutritious ingredients which are reduced during a competition. For instance, Japanese Patent Laid-Open No. Hei 9-1703017 discloses a technique of enhancing physical strength and staying power by supplying trehalose as an energy source for an organism, which becomes insufficient being deficient during physical exercise. Also, an amount of various vitamins consumed increases by the physical exercise or training, and it is known that the vitamin deficiency causes wrong influences to sports performance. Therefore, in order to maintain/improve the sports performance, an athlete is instructed not to neglect the intake of vitamins [*J.J. Sports Sci.*, Vol. 5, No. 3, p. 186-191 (1986)].

Also, there has been disclosed a technique of taking an amino acid preparation for the purpose of improving sports performance. For instance, Japanese Patent Laid-Open No Hei 9-249556 discloses a technique comprising supplying an amino acid composition comprising amino acids contained in saliva secreted from a larva of a wasp in order to supplement the reduction of the blood amino acids accompanied by intense physical exercise, thereby accomplishing improvement in physical exercise functions, alleviation of fatigue and recovery from fatigue after the physical exercise.

There have been reported that branched amino acids (valine, leucine and isoleucine), the main components of proteins in a muscle tissue, are supplied in order to supplement the amino acids consumed by intense training for muscular strength and physical exercises such as long-period endurance race, thereby making it possible to prevent damages of muscle tissues and lowering of muscular strength, to further quickly recover from muscle damages immediately after the physical exercise, and to prevent muscular pain and muscle fatigue [Shokuhin to Kaihatsu (*Foods and Development*), Vol. 34, No. 10, p. 4-8 (1999); Kagaku (*Chemistry*), Vol. 55, No. 6, p. 19-25 (2000)].

Furthermore, there has been known a composition for improving sports performance on the basis of improvement of biological functions. For instance, Japanese Patent Laid-Open No. Hei 11-239465 discloses a technique for enhancing aerobic ability during physical exercise by giving an n-3-based fatty acid as an auxiliary means for improving staying power. Also, Japanese Patent Laid-Open No. 2000-26304 discloses a technique comprising activating the intestinal tract by such effects resulting from *Bifidobacterium* and an oligosaccharide as the amelioration of intestinal microflora, acceleration of mineral absorption, enhancement of immunofunction, and vitamin synthesis, thereby improving sports performance.

Although these techniques can improve the "quantity" aspect such as staying power during physical exercise, they cannot improve "quality" aspect such as mental abilities for suppressing psychological influences in "nervousness (agari)."

Incidentally, there have been known drugs for exciting the central nervous system and stimulating the sympathetic nervous system in order to show maximum abilities in sports and maintain their abilities. These drugs include stimulants such as amphetamine-associated compounds, caffeine, cocaine and ephedrine, narcotic sedatives such as morphine, protein anabolites such as protein-anabolitic steroids and β2 blocking agents, diuretics and peptide hormones, placental gonatropin, adrenocortical hormones, growth hormones, peptide hormones such as erythropoietin, glycoprotein hormones and analogous compounds thereof. However, all of these compounds are dopes and their uses are prohibited.

An object of the present invention is to provide a composition for improving mind-concentration, the composition being able to effectively and safely improve the working efficiency, learning efficiency or the like, or effectively and safely make actual sports performance exhibited, by suppressing (1) psychological influences and/or physical influences caused by various factors during working, learning or the like, or (2) psychological influences in psychogenic physical exercise dysfunctions mainly due to tension, shriveling, lowering or lack of concentration, accumulation of mental fatigue or the like during physical exercise, and a method for improving mind-concentration.

DISCLOSURE OF INVENTION

As a result of intensive studies in order to solve the above-mentioned problems, the present inventors have found that the desired effects are exhibited by theanine contained in green tea, whereby the present invention has been accomplished.

Specifically, the present invention relates to:

[1] a composition for improving mind-concentration, characterized in that the composition comprises theanine;
[2] the composition according to item [1] above, which is used for improving mind-concentration during working or learning;
[3] the composition according to item [1] above, which is used for improving mind-concentration during physical exercise;
[4] the composition according to item [3] above, wherein the composition reduces P wave in brain waves;
[5] the composition according to any one of items [1] to [4] above, wherein the composition is a food composition or a pharmaceutical composition;
[6] a method of improving mind-concentration comprising administering theanine to an individual; and
[7] use of theanine for manufacturing a medicament for improving mind-concentration.

BRIEF DESCRIPTION OF THE DRAWINGS

FIG. 10 is a flow chart showing the procedures for the Preliminary Test of the test for improving mind-concentration in the air rifle shooting.

BEST MODE FOR CARRYING OUT THE INVENTION

Figure 1:
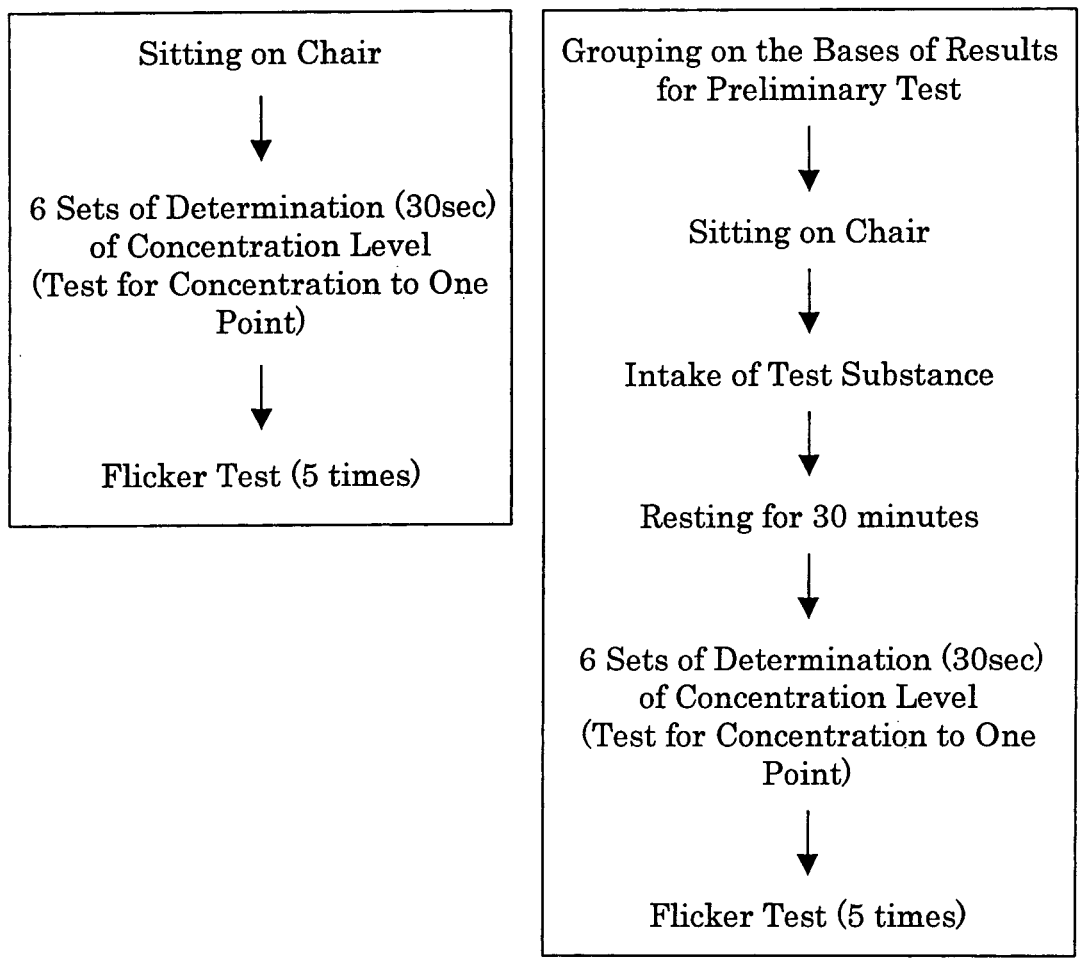
FIG. 1 shows experimental procedures for Preliminary Test and Main Test of the test for improving mind-concentration in one-point concentration.

The composition for improving mind-concentration (hereinafter referred to as "composition") of the present invention is characterized in that the composition comprises theanine. According to the composition, (1) the working efficiency, learning efficiency or the like can be effectively and safely improved by suppressing psychological influences and/or physical influences caused by various factors which acts negatively during working, learning or the like. Also, (2) actual sports performance of an individual can be exhibited by suppressing psychological influences in various psychogenic physical exercise dysfunctions, which negatively act on the exhibition of the sports performance. The exhibition of the desired effects of the composition of the present invention is based on an action for improving mind-concentration found for the first time for theanine contained in the composition.

The term "mind-concentration" as used herein is synonymously used as "concentration," which means the function of focusing the mind on the matter or behavior particularly selected from the acknowledgeable subjects. The term "improving/improvement" means maintenance of the present situation by suppressing the lowering of the desired function, action or the like and/or enhancement of the function, action or the like as compared to the present situation. The term "suppressing/suppression" encompasses cancellation of a specified function, action or the like in addition to suppression of exhibition of a specified function, action or the like.

"Various factors" are not particularly limited, as long as they are factors that can cause some psychological influences and/or physical influences on an individual performing work or the like. Such factors include, for instance, fatigue, continuous working, passage of time, boredom, added age, physiological disorders, emotional disorders, tension, surrounding factors such as vibrations and noises, lack of motivation, demanding attention, compromise, dependence, and the like. Also, "psychological influences" and "physical influences" are not particularly limited, as long as they are psychological and physical influences which are found to have certain cause-and-effect relationships with the factors, respectively.

The term "sports performance" refers to quantitative abilities such as physical strength, technical skills and physical exercise abilities; and qualitative abilities such as information-processing ability such as anticipation and judgment and mental abilities for suppressing psychological influences in various psychogenic physical exercise dysfunctions, their abilities being exhibited during physical exercise. The term "psychogenic physical exercise dysfunctions" refers to embarrassment, sense of shame within self-consciousness, audience anxiety, shyness and the like in the societal situations. The psychogenic physical exercise dysfunctions are, but not particularly limited to, especially, tension and shriveling which are found at a state of "nervousness agari," lowering or lack of concentration due to breakage of "a state of tension (kincho no ito)," accumulation of mental fatigue, and the like. In addition, the term "psychological influences" are not particularly limited, as long as they are mental influences which are recognized to have some sort of cause-and-effect relationships with the above-mentioned psychogenic physical exercise dysfunction.

Theanine used in the present invention is a glutamic acid derivative ($\gamma$-glutamyl ethylamide), and is an amino acid ingredient contained largely in tea leaves naturally. Although an action mechanism of the action for improving mind-concentration by theanine found in the present invention is yet unknown, there has been deduced that theanine gives some sort of actions to any of (1) to (4) below in the brain, thereby exhibiting its action for improving mind-concentration: (1) transmittance of information among nerve cells, (2) biosynthesis or degradation of a neurotransmitter or a precursor thereof, (3) release and incorporation of nerve transmitting substance and (4) an enzyme or coenzyme relating to the above (1) to (3). Also, as to the action of improving mind-concentration during, especially, physical exercise, it is deduced that theanine acts to reduce $\beta$ waves in the brain waves generated during tension, anxieties and the like, so that such an action is exhibited. The composition of the present invention does not have a concern of the generation of adverse actions as seen in the conventional drugs, and can be safely used.

According to the composition of the present invention, the mind-concentration can be improved during working, learning or the like, so that mainly the above-mentioned psychological influences and/or physical influences can be effectively suppressed, whereby working efficiency, learning efficiency or the like can be effectively and safely improved. Also, such an effect has been found to be maintained. Especially, the composition of the present invention is suitable for the improvement of the mind-concentration in a situation where the object to be attained is clear. From this viewpoint, the composition of the present invention is suitable for improving mind-concentration during working or learning. Here, "working" is generally defined as conducting work using the body and the brain, and is not particularly limited as long as it is encompassed by the definition given above. Also "learning" is generally defined as studying and learning, or learning new knowledge or techniques, and is not particularly limited as long as it is encompassed by the definition given above.

In such cases, the exhibition of the action for improving mind-concentration by theanine can be evaluated in accordance with, for instance, Test Example 1 set forth below ((1) determination of state of concentration of attentiveness by attentiveness gauge, and (2) determination of degree of fatigue by flicker test). Also, the exhibition of the action can be similarly evaluated by the instrument of rotary disk follow-up movement (manufactured by Takei Kiki Kogyo K.K.), Uchida-Krepellin mental examination (manufactured by K.K. Nippon Seishin Gijutsu Kenkyusho), and keyboard continuous typing test. In other words, the exhibition of the action for improving mind-concentration by theanine can be evaluated by confirming, for instance, the improvement of accuracy in the work after the intake of theanine as compared to that before the intake of theanine according to the above-mentioned method or the like.

On the other hand, during physical exercise, the psychological influences in various psychogenic physical exercise dysfunctions, which negatively act on the exhibition of sports performance, are suppressed by the improvement of the mind-concentration by the composition of the present invention, whereby actual sports performance can be exhibited. Especially, the composition of the present invention is more suitable for the improvement of the mind-concentration not in mere physical exercises but in competitions performed for the purpose of deciding win or loss. The exhibition of the action for improving mind-concentration of theanine in such cases can be evaluated by a reduction in β wave in comparison of the case where theanine is not administered and the case where theanine is administered, β wave (β1 wave and/or β2 wave) being determined with an electroencephalograph (trade name: MediSyst, manufactured by Linden) in the case where theanine is not administered and in the case where theanine is administered, respectively. Also, the exhibition of the action can be evaluated by the instrument of rotary disk follow-up movement (manufactured by Takei Kiki Kogyo K.K.), an attentiveness gauge (manufactured by Inaba Nigen Kagaku Kogyo), "the instrument of body response type I" (manufactured by Takei Kiki Kogyo K.K.), or pulse rate meter (manufactured by Takei Kiki Kogyo K.K.).

The above-mentioned β wave is one of the waveforms seen in brain waves, and the brain waves are active voltages emitted from cerebral cortex when the brain is active. The brain waves are classified by their frequencies: Those having frequency of 14 to 35 Hz (or 14 Hz or more) are referred to as β wave, those having frequency of 8 to 13 Hz are referred to as a wave, those having frequency of 4 to 7 Hz are referred to as θ wave, those having frequency of 1 to 3 Hz are referred to as δ wave. The β wave is a brain wave observed when there are excessive psychological influences in psychogenic physical exercise dysfunctions. During physical exercise, β wave becomes dominant brain wave as accompanied by "nervousness agari" or fatigue accumulation. In such states, the mind-concentration during physical exercise is hindered, so that actual sports performance cannot be exhibited. The composition of the present invention acts to reduce the β wave generated during physical exercise, so that the psychological influences in psychogenic physical exercise dysfunctions can be suppressed from being in excess. It is deduced that an appropriate vigilance level is maintained by such an action, thereby resulting in the improvement of the mind-concentration.

An appropriate tension is favorable during physical exercise. Also, the vigilance level should be maintained at a certain level in order to maintain physical exercise over a long period of time with sports performance maintained at a certain level. According to the present invention, since an appropriate vigilance level is maintained and the mind-concentration can be improved, not only can anticipation and judgment be calmly made, but also can an ability of physical exercise be exhibited well. Therefore, according to the composition of the present invention, there can be achieved quantitative improvements in addition to qualitative improvements in sports performance, so that actual sports performance of an individual can be effectively, safely and sufficiently exhibited.

Methods for preparing theanine used in the present invention include an organic synthesis method [*Chem. Pharm. Bull.*, 19(7), 1301-1307 (1971)]; a fermentation method (Japanese Patent Laid-Open Nos. Hei 5-68578 and Hei 5-328986); a modification method in which ethylamine in the above method is replaced by an ethylamine derivative such as ethylamine hydrochloride; a method in which pyroglutamic acid is reacted with ethylamine hydrochloride (Japanese Patent Laid-Open No. Hei 9-263573); a plant cell cultivation method (Japanese Patent Laid-Open No. Hei 5-123166); a method of extracting from tea leaves; and the like. From the viewpoints of simplification of preparation steps and costs, the utilization of the fermentation method which can inexpensively obtain theanine in a large amount is preferable. Incidentally, the term "tea leaves" as referred to herein include those of green tea, oolong tea, black tea and the like. Also, a commercially available product [SUNTHEANINE (registered trade mark), manufactured by Taiyo Kagaku Co., Ltd.] may be used.

As theanine, any of L-theanine, D-theanine and DL-theanine can be used, among which the L-form is preferred in the present invention, because it is approved as a food additive, and is economically utilizable. In addition, the theanine used in the present invention may be of any forms, such as purified products, crudely purified products, extracts, and the like.

The theanine content in the composition of the present invention is not particularly limited, and may be properly adjusted as desired. For instance, a favorable theanine content in the composition is preferably from 0.00025 to 100% by weight, more preferably from 0.005 to 100% by weight, and still more preferably from 0.05 to 100% by weight.

A method of detecting theanine in the composition of the present invention is not particularly limited. It is preferable that the method comprises derivatizing in pre-column by orthophthalaldehyde (OPA), separating by high-performance liquid chromatography (HPLC) using ODS column, and detecting and quantifying with a fluorescence detector, or the method comprises separating by HPLC using ODS column, and detecting and quantifying at a wavelength of 210 nm.

The composition of the present invention may further contain various minerals. The composition comprising the mineral is more preferable because there is exhibited a further effect that trace essential elements, and essential elements with tendency to be deficient in living body, can be supplemented. The content of the mineral in the composition is, for instance, preferably from 0.0001 to 99.9% by weight, more preferably from 0.01 to 99.9% by weight. The mineral includes metals essential for maintaining and regulating homeostasis of a living body, such as iron, magnesium, copper, zinc, selenium, calcium, potassium, manganese, chromium, iodine, molybdenum, nickel and vanadium, or metal salts thereof. These can be used alone or in admixture of two or more kinds.

Also, crude medicines, herbs, amino acids, vitamins, and other materials and raw materials which are acceptable in foods may also be contained. These can be used alone or in admixture of two or more kinds.

The crude medicines include, but are not particularly limited to, *Gymnema sylvestra, Garcinia cambogia,* Common valerian, Chinese guta percha, *Angelica acutiloba, Paeonia lactiflora,* peony, *Panax ginnseng,* reisi (*ganoderma*), rehmannia root, and common jujube, and reisi (*ganoderma*), rehmannia root, and common jujube which are effective in stabilizing mind-conditions are preferable.

The forms of the crude medicines may be, but are not limited to, any of extracts, dry products and the like. The herbs include, but are not limited to, anise, carrot seed, clove, coriander, cypress, cinnamon, juniper, ginger, sweet orange, pine needle, basil, patchouli, bitter orange, fennel, black pepper, bay, peppermint, bergamot, mandarin, myrrh, lemongrass, rosemary, grapefruit, cedarwood, citronella, sage, thyme, tea tree, violet leaf, vanilla, hyssop, eucalyptus, lime, lemon, ylang-ylang, cardamon, clary sage, jasmine, geranium, chamomile, Bulgarian rose, rose, olibanum, lavender, chamomile, geranium, sandalwood neroli, verbena, petigrain, vetiver, majoram, lemon balm (*Melissa officinalis*), rosewood, *Hypericum*, St. John's wort, and kawakawa, with preference given to peppermint, bergamot, ylang-ylang, geranium, chamomile, lavender, St. John's wort, and kawakawa, which have sedative and relaxation effects. The forms of these herbs include, but are not limited to, extract, essential oil, and herb tea. The amino acid includes, but are also not particularly limited to, for example, L-form amino acids such as alanine, arginine, arginine acetate, arginine hydrochloride, asparagine, thiotaurine, cysteine, cystine, glutamine, glutamic acid and a salt thereof, glycine, histidine and a salt thereof, hydroxyproline, isoleucine, leucine, lysine and a salt thereof, methionine, ornithine acetate and ornithine hydrochloride, phenylalanine, proline, serine, threonine, tryptophan, tyrosine and valine; DL-form amino acids such as alanine, cysteine and a salt thereof, methionine, phenylalanine, threonine, tryptophan and valine; D-form amino acids such as alanine, cysteine hydrochloride hydrate and phenylalanine; and the like. Also, there are included composite salts of L-amino acids such as those of L-arginine and L-aspargine and mixtures thereof; a metal salt of an amino acid such as potassium aspartate; an ester of an amino acid such as L-ethylcysteine hydrochloride; an acetylamino acid such as acetylcysteine; nucleic acid-associated substances such as adenine and adenosine; omega-amino acid such as β-alanine; an amino acid metabolite such as histamine dihydrochloride; γ-aminobutyric acid, taurine, thiotaurine and hypotaurine. The vitamin includes, but is not particularly limited to, for example, vitamin A, vitamin $B_1$, vitamin $B_2$, vitamin $B_6$, vitamin $B_{12}$, vitamin C, vitamin D, vitamin E, vitamin K, folic acid, nicotinic acid, lipoic acid, pantothenic acid, biotin and ubiquinone, as well as derivatives of these vitamins. The other materials and raw materials which are acceptable in foods include, for example, aloe, royal jelly, melatonin, placenta, propolis, isoflavone, soybean lecithin, egg yolk lecithin, egg yolk oil, chondroitin, cacao mass, collagen, vinegar, chlorella, spirulina, gingko leaf, green tea, tochu tea (*Eucommia ulmoides*), Chinese wolfberry tea, oolong tea, mulberry leaf, *Rubus suavissimus* (tencha), banaba tea, unsaturated fatty acids, functional materials such as saccharides such as oligosaccharides, dietary sweeteners, dietary fibers and soybean peptides, microorganisms such as bifidobacteria and red koji; mushrooms such as *agaricus* (*Agaricus blazei*), Hime *Grifloa frondosa* and *Grifloa frondosa*; fruits such as blueberry, prune, grape, olive, Japanese apricot, and citruses; seeds such as peanut, almond, sesame, and pepper; vegetables such as green pepper, chili, Welsh onion, pumpkin, gourd, carrot, burdock, jute leaf (*Corchorus capsularis*), garlic, perilla, wasabi, tomato, scallion, leaf vegetables, tubers, and beans; seaweeds such as wakame; fishes; meat, poultry, and whale meat; and cereals; as well as their extracts, dried products, crudely purified products, purified products, processed products, and fermented products and the like, among which egg yolk oil, sesame, gingko leaf, and the functional materials such as soybean peptide are preferable.

In addition, as the form of the composition of the present invention, a food composition or a pharmaceutical composition is preferable, from the viewpoint of its suitability for the daily use.

The food composition according to the present invention encompasses not only a food comprising theanine but also a food additive comprising theanine.

Specifically, the above-mentioned food according to the present invention includes a solid food such as dry foods and supplements, and a liquid food such as soft drinks, mineral water, luxury beverages and alcoholic beverages. The solid food includes, but is not particularly limited to, paste products, processed soy products, mousse, jelly, yogurt, cold confectioneries, candies, chocolates, gum, crackers, biscuits, cookies, cake, bread and the like. Also, the liquid food includes, but is not particularly limited to, teas such as green tea, oolong tea, black tea and herb tea, fruit juice concentrates, reconstituted juice concentrates, fresh juices, mixed fruit juices, fruit grain-containing fruit juice, fruit juice-containing beverages, mixed fruit/vegetable juice, vegetable juice, mineral water, carbonated beverages, soft drinks, milk, milk beverage, Japanese sake, beer, wine, cocktails, shochu, whiskey, and the like.

In addition, the pharmaceutical composition of the present invention is not particularly limited as long as the pharmaceutical composition comprises theanine. For instance, the pharmaceutical composition may be any of solutions, suspensions, powders, solid molded products and the like without being particularly limited thereto. Therefore, the preparation forms of the pharmaceutical composition include tablets, capsules, powdered agents, granules, health care drinks and the like. The pharmaceutical composition can also be used in combination with other medicaments.

A process for preparing the composition of the present invention is not particularly limited, and there can be used general processes for preparation of a food or a medicament such as a process of powder-mixing theanine and other raw materials; a process of dissolving theanine and other raw materials in a solvent to give a mixed solution; and a process of freeze-drying the mixed solution; a process of spray-drying the mixed solution. The components other than theanine which can be used when the composition of the present invention is prepared can be selected appropriately in accordance with the desired use, so long as the exhibition of the desired effects by the theanine is not inhibited.

For instance, the food composition of the present invention can be prepared by adding theanine to the conventional food by a conventional method so that the content of theanine in the food composition of the present invention after the preparation is preferably within the above-mentioned range of the preferred content of theanine in the composition. In addition, the pharmaceutical composition of the present invention can be prepared by formulating theanine by a conventional method, together with, for instance, a known organic or inorganic vehicle suitable for oral administration, excipient, binder, stabilizing agent, and the like, so that the content of theanine in the pharmaceutical composition of the present invention is preferably within the above-mentioned range of the preferred content of theanine in the composition as in the case of preparation of the food composition. Use of theanine in the manufacturing of the medicament for improving mind-concentration is also provided as one embodiment of the present invention.

Further, in one embodiment of the present invention, there is provided a method for improving mind-concentration, comprising administering theanine to an individual. According to the method, since the mind-concentration of the individual can be improved safely and effectively, without any concerns on the generation of adverse action, the method is effective for improving working efficiency or learning efficiency, or making actual sports performance of the individual exhibited. Especially, the method is suitable for the improvement of the mind-concentration in a situation where the object to be attained is clear. From this viewpoint, the method is especially suitable for improving mind-concentration during working or learning. In addition, the method is suitable for the improvement of the mind-concentration not in mere physical exercises but in competitions performed for the purpose of deciding win or loss. Here, the term "individual" refers to, for instance, a mammal, concretely human, a horse, a dog, and the like, among which the method of the present invention can be suitably used for human.

In this embodiment, in general, as the effective dosage of theanine for obtaining the desired effects of the present invention, in a case of a human, the dosage is, for instance, preferably from 0.01 to 200 mg/kg weight, more preferably from 1 to 20 mg/kg weight per one dose. However, since there are some differences (age, sex and the like) between individuals, the dosage of theanine in the present invention is not limited only to those ranges given above. The dosage of the theanine may be appropriately adjusted depending upon the kinds of performed working, learning or the like in order to obtain working efficiency, learning efficiency or the like desired for each individual, or depending upon each performed physical exercise with different optimal vigilance level required between the kinds in order to obtain sports performance desired for each individual.

In order to administer theanine, there may be used theanine per se, or the composition of the present invention, preferably the food composition or pharmaceutical composition. Also, the administration methods, the number of administration, the administration period, and the like are also not particularly limited. For instance, the theanine may be administered within the above-mentioned effective dosage range at once or divided in plural times, preferably by oral administration, to the above-mentioned individual, preferably human. The theanine or the composition of the present invention can be administered, for instance, before work, preferably 5 to 90 minutes before work, so that the working efficiency can be effectively improved. The administration during work is effective for maintaining the working efficiency. The theanine or the composition of the present invention can be also effectively taken on a daily basis in case the theanine or the composition is required to be taken. On the other hand, the theanine or the composition of the present invention can be administered before physical exercise, preferably from 15 to 30 minutes before physical exercise, whereby the sports performance during physical exercise can be efficiently improved. The theanine or the composition can be administered during physical exercise, whereby the improvement of the sports performance can be maintained. The theanine or the composition of the present invention can be also effectively taken on a daily basis in case the theanine or the composition is required to be taken.

The exhibition of the desired effects by theanine used in the present invention is irrelevant to various properties required in an individual which are different depending upon work, learning or the like of the individual, such as comprehension, memorization and skills. Therefore, the improvements of efficiencies are brought about in all sorts of work, learning and the like. For instance, the work includes, but is not limited to, driving an automobile or the like, playing a musical instrument or the like, conversation, presentation, calculation, typing a keyboard, work and examination of a product in a manufacturing line in a plant, and the like, and the learning includes, but is not limited to, doing various drills, reading a book, acquiring a technique or skill, and the like.

Especially, it is considered that the results are greatly influenced by the psychological influences and/or the physical influences on an individual as compared to those of daily work or the like when an individual is assigned as a task of carrying out a certain business within a given time frame, or when an individual is in a situation where an object to be attained is clearer, such as important presentation before a public audience, and an entrance examination. Therefore, the intake of theanine before and/or during work or the like will be selective. Each individual can realize, for instance, alleviation of fatigue, improvement and maintenance of concentration, reduction of mistakes, and the like during working, learning or the like with the improvement of the mind-concentration. Also, the work, the learning or the like can be carried out accurately and rapidly.

The exhibition of the desired effects by theanine used in the present invention is irrelevant to various exercise abilities required in an individual which are different depending upon each of individual physical exercises, such as staying power, instantaneous power, sense of balance. Therefore, the composition of the present invention is effective for all sorts of physical exercises. For instance, the physical exercise includes track and field athletics such as short distance, middle distance, relay, marathon, race waking, high jump, pole-vault, shot put, javelin throw and hammer throw; aquatics such as swim race, diving, synchronized swimming and water polo; ball games such as basketball, tennis, volleyball, handball, soccer (football), field hockey, softball, baseball, table tennis, beach volleyball, golf, Rugby football, American football, lacrosse, bowling, gate ball, dodge ball and billiards; gymnastics such as trampoline and rhythmic gymnastics; fighting sports such as boxing, fencing, judo, taekwondo, wrestling, karate, Nippon kenpo, aikido, kendo and sumo; competitions of shooting a target, such as rifle shooting, archery and Japanese bow shooting; horsemanship, bicycle race, motor cycle race, automobile race and the like; aquatic sports such as rowing, sailing and canoeing; competitions on ice and snow, such as skating, ice hockey, skiing, ski jump, snowboard and snowball fight; badminton, weight lifting, Sepatakraw and the like, without intending to limit to these alone.

In the various physical exercises mentioned above, especially, it is thought that in a sport which is purposed to decide win or loss, not mere a physical exercise, psychological influences on an athlete greatly influences the results, as compared to those of the daily physical exercise, so that it is effective to take theanine before and/or during the competition. With the improvement of the mind-concentration, an athlete can, for instance, realize that a reaction time period until the start after hearing the signal for starting is shortened in the track and field athletics (short distance), that pleasant and refreshing feelings are maintained with little sense of fatigue for a physical exercise over a long period of time in the track and field athletics (long distance) and long-distance swimming, and that the shriveling of hands and nervousness agari are prevented in a situation of shooting a target in the rifle shooting, the archery, the Japanese bow shooting and the like. Also, in a team sport such as soccer (football), volleyball or handball, the attention is paid always to the positions and the movements of the players of the opponent and the teammates, so that anticipation and judgment can be more accurately and rapidly carried out.

The theanine used in the present invention has high safety. For instance, in an acute toxic test using a mouse, there are no cases of death with an oral administration at 5 g/kg, and there are found no abnormalities in the general states, weight and the like. Also, especially L-theanine is known as a main component of umami (tastiness) of the green tea, and is also used as a food additive giving umami, without the limitation of its added amount under the regulation for food hygiene. Moreover, contrary to the conventional drugs, since there is no adverse action by theanine at all, the mind-concentration is safely and effectively achieved according to the composition of the present invention, whereby working efficiency, learning efficiency or the like, or sports performance can be improved.

The present invention will be further described by means of Examples and Test Examples, without intending to limit the scope of the present invention to these Examples and Test Examples alone. Here, in the preparation of each composition described hereinbelow, L-theanine [trade name: Suntheanine, manufactured by Taiyo Kagaku Co., Ltd.] was used. Also, unless specified otherwise, "parts" represent "parts by weight."

Preparation Example 1 Preparation of Theanine by Enzymatic Method

The amount 21.9 g of glutamine and 28.5 g of ethylamine were allowed to react at 30° C. for 22 hours in 0.5 L of 0.05 M borate buffer (pH 9.5) in the presence of 0.3 U glutaminase (manufactured by Amano Enzyme Inc.). Thereafter, the reaction mixture was subjected to column chromatography using Dowex 50×8 column and Dowex 1×2 column (both manufactured by Muromachi Kagaku Kogyo K.K.), and thereafter the resulting product was treated with ethanol, thereby isolating a desired product from the reaction mixture.

The identification of the obtained substance as L-theanine was carried out by subjecting the isolated substance to amino acid analyzer and paper chromatography, whereby confirming that the isolated substance exhibits the same behaviors as the standard substance. Moreover, when the isolated substance was subjected to hydrolysis treatment with hydrochloric acid or glutaminase, glutamic acid and ethylamine were generated at a ratio of 1:1 (molar ratio). As described above, since the isolated substance was hydrolyzed by glutaminase, it was shown that ethylamine was bonded at the γ-position of glutamic acid. In addition, it was also confirmed by using the glutamic acid dehydrogenase that glutamic acid generated by hydrolysis had an L-form. From the above, the resulting isolated substance was finally confirmed to be L-theanine. By the above procedure, 8.5 g of L-theanine was obtained.

Preparation Example 2 Extraction of L-Theanine from Tea Leaves

Ten kilograms of tea leaves (*Camellia sinensis* L.) were subjected to extraction with boiling water. The resulting extract was then applied to a cationic exchange resin ("Dowex HCR W-2," manufactured by Muromachi Kagaku Kogyo K.K.), and eluted with 1 N NaOH. The eluted fraction was applied to an activated carbon ("Taiko Kasseitan SG" manufactured by Futamura Kagaku Kogyo K.K.), and eluted with 15% ethanol. The resulting eluted fraction was concentrated with an RO membrane ("NTR 729 HF" manufactured by NITTO DENKO CORPORATION). Thereafter, the concentrate was purified by column chromatography. Furthermore, the purified product was recrystallized, to give 24.8 g of L-theanine.

Example 1 Preparation of Theanine-Formulated Tablet

As one example of a theanine-formulated composition, a theanine-formulated tablet (250 mg/tablet) was prepared by mixing L-theanine with other raw materials given below, and tabletting the resulting mixture.

| | |
|---|---|
| L-Theanine | 20 parts |
| Crystalline Cellulose | 5 parts |
| Reducing Maltose | 20 parts |
| Lactose | 50 parts |
| Aspartame | 1 part |
| Sucrose Fatty Acid Ester | 4 parts |
| Silicon Dioxide | 0.5 parts |
| Total | 100.5 parts |

Comparative Example 1 Preparation of Control Tablet

Raw materials given below were mixed, and the mixture was tableted, to give a control tablet (250 mg/tablet).

| | |
|---|---|
| Crystalline Cellulose | 5 parts |
| Reducing Maltose | 20 parts |
| Lactose | 70 parts |
| Aspartame | 1 part |
| Sucrose Fatty Acid Ester | 4 parts |
| Silicon Dioxide | 0.5 parts |
| Total | 100.5 parts |

Example 2 Preparation of Theanine-Formulated Candy

As one example of a theanine-formulated composition, a theanine-formulated candy (5.2 g/piece) was prepared using L-theanine in accordance with the following composition.

| | |
|---|---|
| Granulated Sugar | 64 parts |
| Malt Syrup | 23 parts |
| L-Theanine | 3 parts |
| Flavor (Lemon Flavor) | 0.05 parts |
| Tartaric Acid | 1 part |
| Water | 30 parts |
| Total | 128.05 parts |

The granulated sugar was completely dissolved in 20 parts of water with heating to 110° C. The malt syrup was added thereto, and the temperature was raised to 145° C. After heating was stopped, tartaric acid was added thereto and mixed, and the remaining water in which L-theanine was previously dissolved was added thereto. The mixture was mixed again, cooled to 75° to 80° C., and formed with a molding roller. The content of L-theanine in each drop of candy was determined. As a result, its content was 202 mg/g of drop.

Example 3 Preparation of Theanine-Formulated Blueberry Juice

As one example of a theanine-formulated composition, a theanine-formulated blueberry juice was prepared using L-theanine in accordance with the following composition.

| | |
|---|---|
| Fructose Sucrose Solution | 12 parts |
| Blueberry Concentrate Juice | 1 part |
| 1/5 Transparent Lemon Juice | 0.4 parts |
| Sodium Citrate | 0.05 parts |
| L-Theanine | 0.1 parts |
| Flavor (Blueberry Flavor) | 0.07 parts |
| Water | 86.4 parts |
| Total | 100.02 parts |

Each of components except for the flavor and water was mixed with each other with stirring to dissolve the components. The pH of the resulting solution was adjusted to 3.1 by using sodium citrate (crystals). Next, the flavor and water were added to the resulting solution, and the temperature was raised to 95° C. The solution was filled and then cooled. The content of L-theanine in the blueberry juice was determined. As a result, its content was 98.3 mg/100 ml.

Example 4 Preparation of Theanine-Formulated Grapefruit Juice

As one example of a theanine-formulated composition, a theanine-formulated grapefruit juice was prepared using L-theanine in accordance with the following composition.

| | |
|---|---|
| Fructose Sucrose Solution | 6 parts |
| L-Theanine | 0.1 parts |
| Ferric Pyrophosphate | 0.06 parts |
| Placenta Extract | 0.01 parts |
| 100% Grapefruit Juice | 30 parts |
| Water | 63.92 parts |
| Total | 100.09 parts |

Each of the above-mentioned components was mixed with each other with stirring to dissolve the components. The pH of the resulting solution was adjusted to 3.1 by using sodium citrate (crystals). Next, the temperature was raised to 95° C., and the solution was filled and then cooled. The content of L-theanine in the grapefruit juice was determined. As a result, its content was 99.9 mg/100 ml.

Test Example 1 Test for Improving Mind-Concentration in Concentration to One Point For each of the cases where the theanine-formulated tablet prepared in Example 1 and the control tablet prepared in Comparative Example 1 were taken as test substances, 1) the determination of the concentration level by concentration level meter and 2) the determination of the degree of fatigue by flicker test were carried out in the following tests.

[I] Test Methods
(1) Subjects: 44 female university students (ages 18-23 years old), average weight: 50.8 kg
(2) Environmental conditions: laboratory (room temperature: 23-26° C., humidity 47-65%)
(3) Determination Contents and Determination Methods:
　i) Determination of Concentration Level (Test for Concentration to One Point)

The concentration level was determined by using a concentration level meter Model AF (manufactured by Inaba Tech. Inst.). In this equipment, any of numerical figures 1 to 9 randomly appears on the screen at a rate of 2 Hz. The subject is asked to carefully watch the numerical figures appearing on the screen (concentration to one point), and press a switch when any of the three numerical figures previously designated appear on the screen. Whether or not the subject is in excellent concentration level is judged by the accuracy of such a response. Specifically, the accuracy of the response is obtained as a percentage of correct responses, and the percentage is regarded as a record for the concentration to one point. The concentration level is evaluated in accordance with the record. The higher the record is, the more excellent the concentration level is. The percentage of correct responses (%) is calculated by the following equation:

Percentage of Correct Responses $(\%)[[S-(P+M)]/S] \times 100$ wherein S is the number of "Signal" (the number of transmitted signals), P is the number of "Pass" (the number of the numerical figures which are mistakenly overlooked), and M is the number of "Miss" (the number of the numerical figures which are mistyped).

ii) Determination of Degree of Fatigue

When the same work is repeated for a certain length of time, the working efficiency lowers even if a subject thinks he is working in the same manner. In order to determine the degree of fatigue (visual fatigue), which serves as an index for such a lowered efficiency, flicker test was conducted. In the flicker test, a digital flicker (manufactured by Takei Kiki Kogyo K.K.) is used. A flicker value is obtained based on a boundary frequency (movement factor) found between the frequency of flickering light and the frequency of continuous light, and the degree of fatigue is judged by the size of the flicker value. In other words, the smaller the flicker value is, the larger the degree of fatigue is.

(4) Experimental Procedures

The test was constructed by two stages: Preliminary Test and Main Test.

i) Preliminary Test

Six sets of the determinations of the concentration level (test for concentration to one point) were carried out. The test was carried out with the subject sitting on a chair in the laboratory. The concentration level meter was set so that the distance between the screen for numerical figures and the eyes of the subject was 1 m. Also, 5 sets of the flicker test were conducted.

ii) Main Test

Each of the subjects was divided into two groups with equal level, a test group and a control group, each composed of 22 subjects, on the bases of the records for the concentration to one point in the Preliminary Test. The test group was allowed to take one tablet of the theanine-formulated tablet prepared in Example 1 (amount of L-theanine: 50 mg), and the control group was allowed to take one tablet of the control tablet prepared in Comparative Example 1, and thereafter to rest for 30 minutes, respectively. Here, during the test, each subject was not informed of which test substance the subject was allowed to take.

Next, the determination of the concentration level (test for concentration to one point) was conducted, and thereafter the flicker test was conducted. The experimental procedures for the Preliminary Test and the Main Test are shown in FIG. 1.

[II] Results
(1) Comparison of Records for Concentration to One Point

Figure 2:
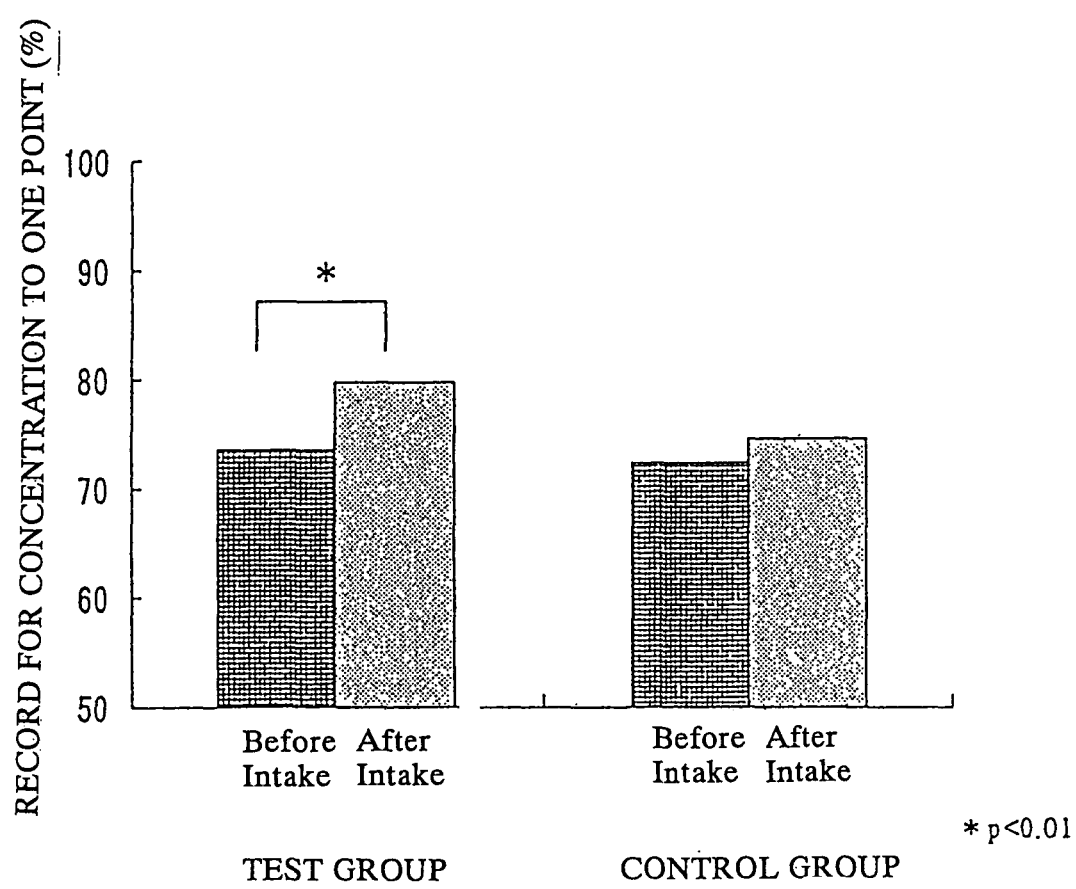
FIG. 2 is a bar chart showing the record for the one-point concentration (average value) of the subjects (for each group) in the one-point concentration. In the chart, each bar shows the record for the one-point concentration. The statistic processing was conducted by Student paired t-test.

The comparison of the records for the concentration to one point (average value of 22 subjects of each group) before and after the intake of the test substance in the test group and the control group is shown in FIG. 2. A substantial difference could not be found in the records for the concentration to one point of each of the two groups before the intake of the test substance, namely the records for each of the two groups in the Preliminary Test, because the subjects were divided into the two groups so that the records for the concentration to one point were almost the same level between the two groups on the bases of the entire subjects' records. In the two groups, a substantial difference could not be also found in the flicker test. On the other hand, after the intake of the test substance, namely in the Main Test, the record for the concentration to one point was improved in the test group as compared to that of the control group. Also, when the records were compared before and after the intake of the test substance in each group, a significant improvement in the records was found in the test group ($p<0.01$), while a notable difference could not be found in the control group.

As described above, since the records for the concentration to one point improve with the intake of the theanine-formulated tablet, as compared to that of the intake of the control tablet, it is seen that the concentration level improves by the intake of theanine.

(2) Study on Degree of Fatigue on Bases of Flicker Values

Figure 3:
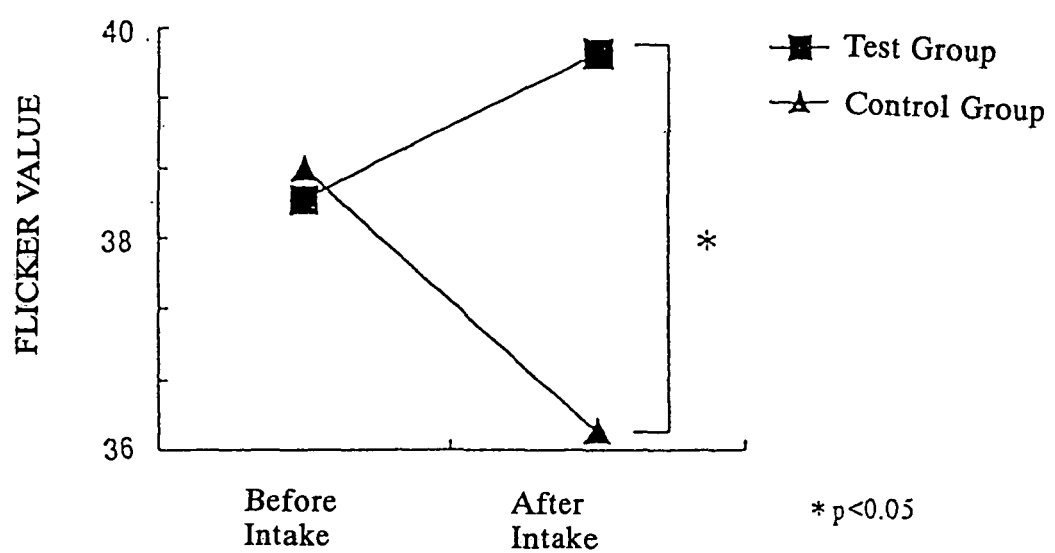
FIG. 3 is a linear graph showing the flicker value (average value) of the subjects (for each group) in the flicker test. The statistic processing was conducted by Student paired t-test.

The comparison of the flicker values (average value of 22 subjects of each group) before and after the intake of the test substance in the test group and the control group is shown in FIG. 3. The flicker values were obtained by the flicker tests in the Preliminary Test before the intake of the test substance and in the Main Test after the intake of the test substance.

As shown in FIG. 3, after the intake of the test substance, the flicker values were significantly higher in the test group as compared to that of the control group ($p<0.01$). Therefore, it is seen that when the same work is performed, the degree of fatigue is alleviated by the intake of the theanine.

Test Example 2 Test for Improving Mind-Concentration During Reading

A questionnaire survey was conducted regarding the concentration during reading for each of the cases where the theanine-formulated candy prepared in Example 2 and the control candy separately prepared by replacing L-theanine contained in the candy with lactose were taken as test substances.

(1) Method of Survey

The questionnaire survey was conducted for 2 days. Subjects were divided into two groups of Group A and Group B (each group composed of 12 each of males and females, a total of 24 subjects; average age: male: 36.2 years old, female: 24.3 years old; average body weight: male: 64.2 kg, female: 52.8 kg). Group A was allowed to take the theanine-formulated candy on Day 1 of the beginning of the survey, and the control candy on Day 2, while Group B was allowed to take the control candy on Day 1 and the theanine-formulated candy on Day 2, each candy being taken one drop per day at the same hour and the same location. The amount of intake of L-theanine for each subject was 202 mg. During the survey period, each subject was not informed of which the test substance the subject was allowed to take.

Each subject was asked to read a book over a period of 1 hour starting from 30 minutes after the intake of the test substance. Each subject was allowed to read the same book for the two-day survey. On Day 2, the subject was asked to read the continuation of the portion of Day 1. After termination of reading, the subject was asked to fill in the questionnaire regarding the concentration. The questionnaire consisted of the following two question items. The subjects were asked to select any one of the four choices also given below in each question item.

(Question Items of Questionnaire)
1. Extent of Concentration
"could considerably concentrate," "could concentrate," "not changed" and "could not concentrate"
2. Maintenance of Concentration
"could considerably maintain," "could maintain," "not changed" and "could not maintain"

(2) Results

Figure 4:
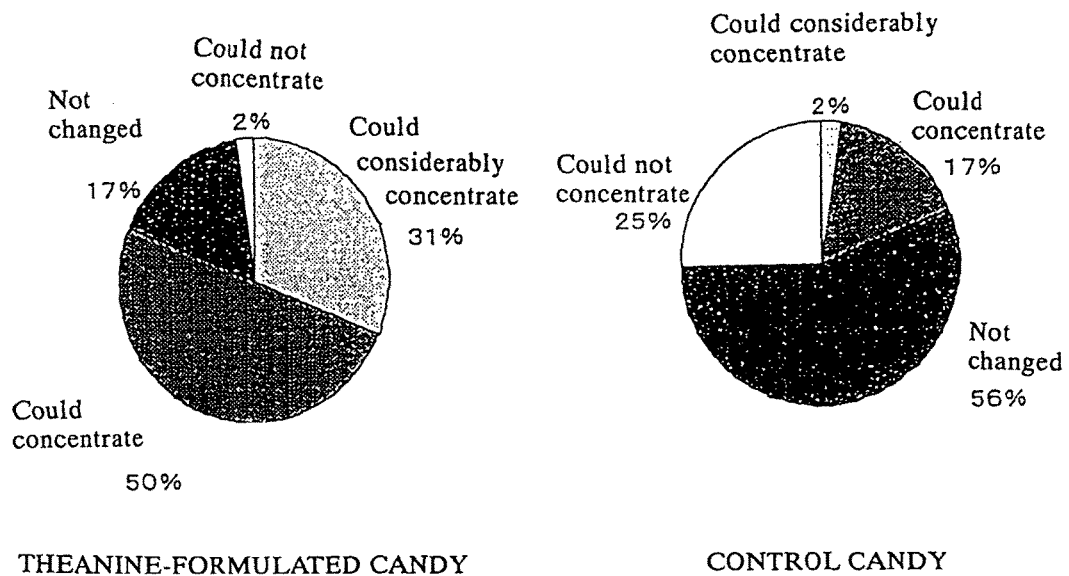
FIG. 4 is a pie chart showing the questionnaire totaling results on the extent of concentration of the subjects during reading.
Figure 5:
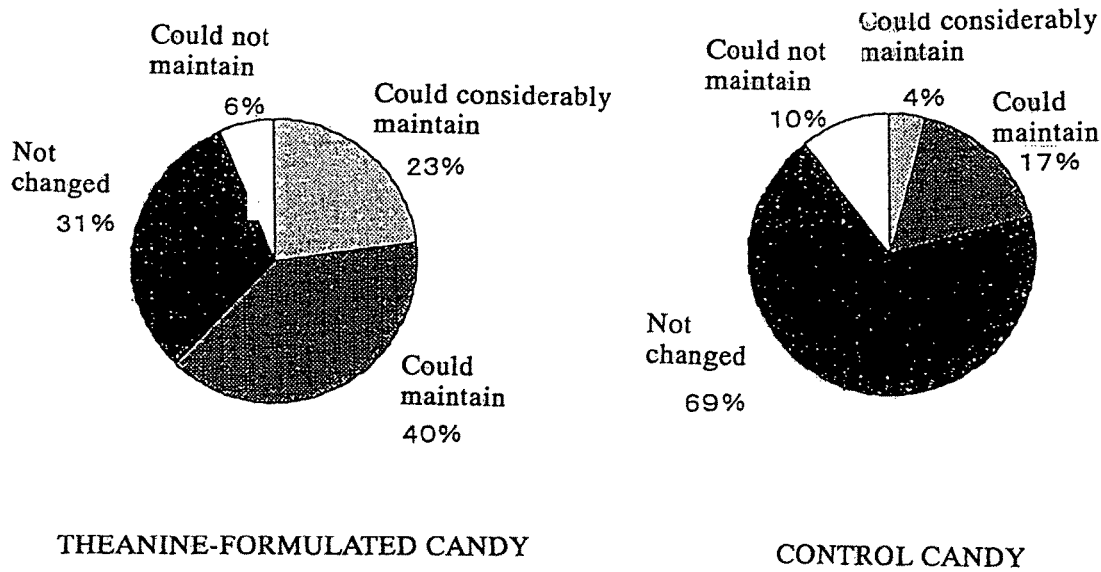
FIG. 5 is a pie chart showing the questionnaire totaling results on the maintenance of concentration of the subjects during reading.

The questionnaire results were totaled on the bases of the entire results (n=48) obtained in Group A and Group B for each test substance. FIGS. 4 and 5 show total results of the questionnaire after reading.

i) Extent of Concentration

The results are shown in FIG. 4. While those responding as "could considerably concentrate" and "could concentrate" were 19% in the intake of the control candy, those in the intake of the theanine-formulated candy, the composition of the present invention, were 81%.

ii) Maintenance of Concentration

The results are shown in FIG. 5. While those responding as "could considerably maintain" and "could maintain" were 21% in the intake of the control candy, those in the intake of the theanine-formulated candy, the composition of the present invention, were 63%.

It is seen from the above that the concentration is improved and maintained during reading by the intake of the composition of the present invention.

Test Example 3 Test for Improving Mind-Concentration in Keyboard Continuous Typing Test A keyboard continuous typing test was conducted with 12 male and female adults usually using a personal computer in business (average age: male: 31.6 years old, female: 27.3 years old; average body weight: male: 63.8 kg, female: 51.2 kg) as subjects for each of the cases where the theanine-formulated grapefruit juice prepared in Example 4 and water were continuously taken as test substances.

In the test, the subjects were divided into two groups (Group a: 2 males and 4 females; Group b: 2 males and 4 females). On Day 1 of the beginning of the test to Day 5, Group a was allowed to take the theanine-formulated grapefruit juice at 200 ml/day, and Group b was allowed to take water at 200 ml/day. Also, on Day 7 to Day 11, Group b was allowed to take the theanine-formulated grapefruit juice at 200 ml/day, and Group a was allowed to take water at 200 ml/day. Here, the amount of L-theanine taken for each subject was 200 mg. During the test period, each subject was not informed of which the test substance the subject was allowed to take.

Keyboard continuous typing test was conducted under the conditions that the subjects typed the keyboard as usual without any loads. The test was conducted on the day before the beginning of the test, and Day 6 and Day 12 after the beginning of the test. General sentences in contemporary languages were typed for a time limit of 10 minutes. The amount of work for each subject was calculated by scoring 1 point for each character typed, and scoring −1 point for each mistyped character (level of The Third Grade of Nippon Word-Processing Testing Association).

Figure 6:
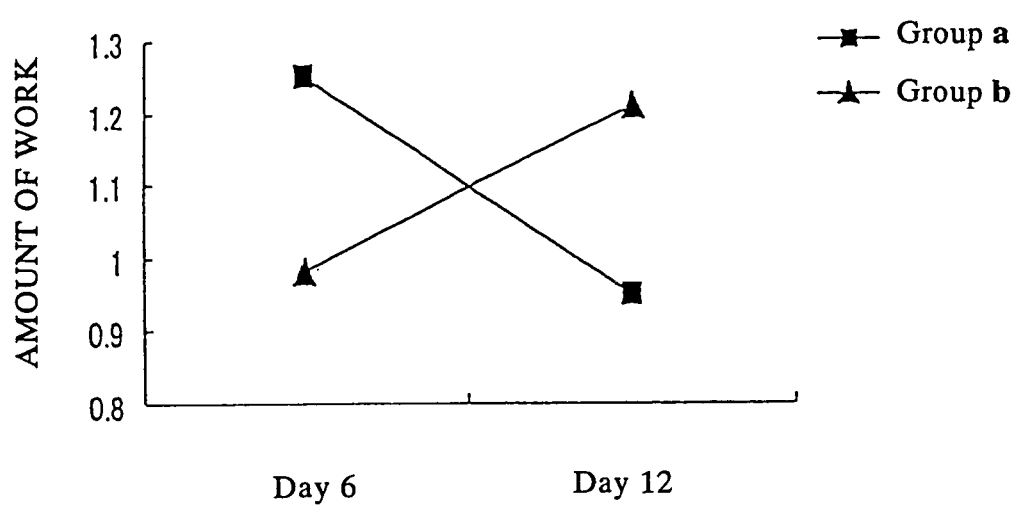
FIG. 6 is a linear graph showing the amount of work (average value) of the subjects (for each group) in the keyboard continuous typing test. The numerical figures on the axis of abscissa shows the number of days after the beginning of the test.

The comparison of the amount of work (average value of 6 subjects for each group) in Group a and Group b is shown in FIG. 6. Here, since there is great difference in the amount of work among the subjects, the amount of work is expressed as a ratio to the value of the day before the beginning of the test in FIG. 6, the value being defined as 1. As shown in FIG. 6, the amount of work increased in the case where the theanine-formulated grapefruit juice was continuously taken (the results of Day 6 of Group a and Day 12 of Group b), as compared to the case where water was continuously taken (the results of Day 12 of Group a and Day 6 of Group b). Thus, it is seen that the concentration improves during work by continuously taking the composition of the present invention.

Example 5 Preparation of Theanine-Formulated Chewable Tablet

As one example of a theanine-formulated composition for improving mind-concentration, the raw materials given below were mixed, and tableted, to prepare a theanine-formulated chewable tablet.

| | | |
|---|---|---|
| Frosted Sugar | 71.67% by weight | (1.075 g) |
| Trehalose | 10% by weight | (0.15 g) |
| L-Theanine | 13.33% by weight | (0.2 g) |
| Sucrose Fatty Acid Ester | 1% by weight | (0.015 g) |
| Flavor (manufactured by TAKASAGO INTERNATIONAL CORPORATION) | 4% by weight | (0.06 g) |
| Total | 100% by weight | (1.5 g) |

Specifically, each of the raw materials was mixed in accordance with the above-mentioned composition, and the mixture was granulated. Thereafter, the granulated product was tableted so as to be 1.5 g per each tablet.

Comparative Example 2 Preparation of Control Chewable Tablet

The raw materials given below were mixed, and tableted, to prepare a control chewable tablet.

| | | |
|---|---|---|
| Frosted Sugar | 85% by weight | (1.275 g) |
| Trehalose | 10% by weight | (0.15 g) |
| Sucrose Fatty Acid Ester | 1% by weight | (0.015 g) |
| Flavor (manufactured by TAKASAGO INTERNATIONAL CORPORATION) | 4% by weight | (0.06 g) |
| Total | 100% by weight | (1.5 g) |

Specifically, each of the raw materials was mixed in accordance with the above-mentioned composition, and the mixture was granulated. Thereafter, the granulated product was tableted so as to be 1.5 g per each tablet.

Example 6 Preparation of Theanine-Formulated Chewing Gum

As one example of a theanine-formulated composition for improving mind-concentration, the raw materials given below were mixed, to prepare a theanine formulated chewing gum.

| | | |
|---|---|---|
| Gum Base | 20% by weight | (0.7 g) |
| Grinded Sugar | 74.3% by weight | (2.6 g) |
| L-Theanine | 5.7% by weight | (0.2 g) |
| Total | 100% by weight | (3.5 g) |

The above-mentioned raw materials were mixed and kneaded until the mixture became homogeneous. The resulting kneaded product was extruded with an extruder into a sheet-like form, with keeping the temperature at 50° C., and further pressed with a pressure roller into a sheet having a given thickness. The sheet was cut into a size of 20 mm×75 mm, to produce a chewing gum of 3.5 g per piece.

Comparative Example 3 Preparation of Control Beverage

Each of the raw materials was mixed in accordance with the formulation given below, and the components were dissolved and filled in a can so as to have an amount 330 g per can, and the can was sterilized, to prepare a control beverage.

| | | |
|---|---|---|
| Fructose | 1% by weight | (3.3 g) |
| Muscat Juice | 0.1% by weight | (0.33 g) |
| Vitamin C | 0.2% by weight | (0.66 g) |
| Granulated Sugar | 0.01% by weight | (0.33 g) |
| Citric Acid | 0.1% by weight | (0.33 g) |
| Water | 98.59% by weight | (325.347 g) |
| Total | 100% by weight | (330 g) |

Example 7 Preparation of Beverage Containing 50 Mg of Theanine

Each of the raw materials was mixed in accordance with the formulation given below, and the components were dissolved and filled in a can so as to have an amount 330 g per can, and the can was sterilized, to prepare a beverage containing 50 mg of theanine.

| | | |
|---|---|---|
| Fructose | 1% by weight | (3.3 g) |
| Muscat Juice | 0.1% by weight | (0.33 g) |
| Vitamin C | 0.2% by weight | (0.66 g) |
| Granulated Sugar | 0.01% by weight | (0.33 g) |
| Citric Acid | 0.1% by weight | (0.33 g) |
| L-Theanine | 0.015% by weight | (0.05 g) |
| Water | 98.575% by weight | (325.297 g) |
| Total | 100% by weight | (330 g) |

Example 8 Preparation of Beverage Containing 200 Mg of Theanine

Each of the raw materials was mixed in accordance with the formulation given below, and the components were dissolved and filled in a can so as to have an amount 330 g per can, and the can was sterilized, to prepare a beverage containing 200 mg of theanine.

| | | |
|---|---|---|
| Fructose | 1% by weight | (3.3 g) |
| Muscat Juice | 0.1% by weight | (0.33 g) |
| Vitamin C | 0.2% by weight | (0.66 g) |
| Granulated Sugar | 0.01% by weight | (0.33 g) |
| Citric Acid | 0.1% by weight | (0.33 g) |
| L-Theanine | 0.061% by weight | (0.2 g) |
| Water | 98.529% by weight | (325.147 g) |
| Total | 100% by weight | (330 g) |

Example 9 Preparation of Granule

There were mixed lactose (5 g), L-theanine (10 g), granulated sugar (3 g), flavor (2 g, manufactured by TAKASAGO INTERNATIONAL CORPORATION), vitamin C (15 g) and starch (20 g), and granulated, to prepare a granule, so that each granule was packed and wrapped to be 2 g per package.

Example 10 Preparation of Powdery Beverage

There were mixed powdered green tea (50 g), L-theanine (10 g), granulated sugar (3 g), grinded sugar (20 g), vitamin C (10 g) and citric acid (1 g), and granulated, to prepare a powdery beverage of powdered green tea, so that each powdery beverage was packed and wrapped to be 2 g per package.

Example 11 Preparation of Chocolate

There were mixed cacao mass (60 g), L-theanine (10 g), granulated sugar (3 g), trehalose (9 g), glycerol fatty acid ester (0.9 g), whole powdered milk (10 g), and vegetable oil (10 g), to prepare a chocolate by a conventional method.

Test Example 4 Test for Improving Mind-Concentration in Japanese Bow Shooting

The subjects were 30 female university students belonging to Japanese bow shooting club (average age: 20.1, average weight: 49.3 kg). The grades (dan) and the experience in the number of years of Japanese bow shooting for the subjects are shown in Table 1 and 2.

TABLE 1

Grades (Dan) in Japanese Bow Shooting of Subjects

| Grades (Dan) | Number of Subjects |
| --- | --- |
| Fourth Grade (yon-dan) | 2 |
| Third Grade (san-dan) | 8 |
| Second Grade (ni-dan) | 6 |
| First Grade (sho-dan) | 14 |
| Total | 30 |

TABLE 2

Experience in Number of Years of Subjects

| Experience in Number of Years | Number of Subjects |
| --- | --- |
| Five to Six Years | 6 |
| Four to Five Years | 3 |
| Two to Three Years | 13 |
| One to Two Years | 8 |
| Total | 30 |

(1) Preliminary Test
 i) Method
First, a preliminary test was conducted. In the test, each subject performed bow shooting in a standing position at a shooting hall, and target hit scores were recorded by a recorder. After completion of the all the matches, a questionnaire survey was conducted for each series of shots on the subjective concentration on an 10-rank scale from 0 point for "could not concentrate at all" to 10 points for "could concentrate very much", or the subjective tension on another 10-rank scale from 0 point for "not tense at all" to 10 points for "very tense".
 ii) Results
Although the results of the preliminary test showed differences in target hit scores among the subjects according to grades (dan) and experience in the number of years of Japanese bow shooting, there were no particular significant differences in the tension and the concentration. Thus, the tension and the concentration were found to be at the same level among the subjects, although there were some differences in their skills.

Figure 7:
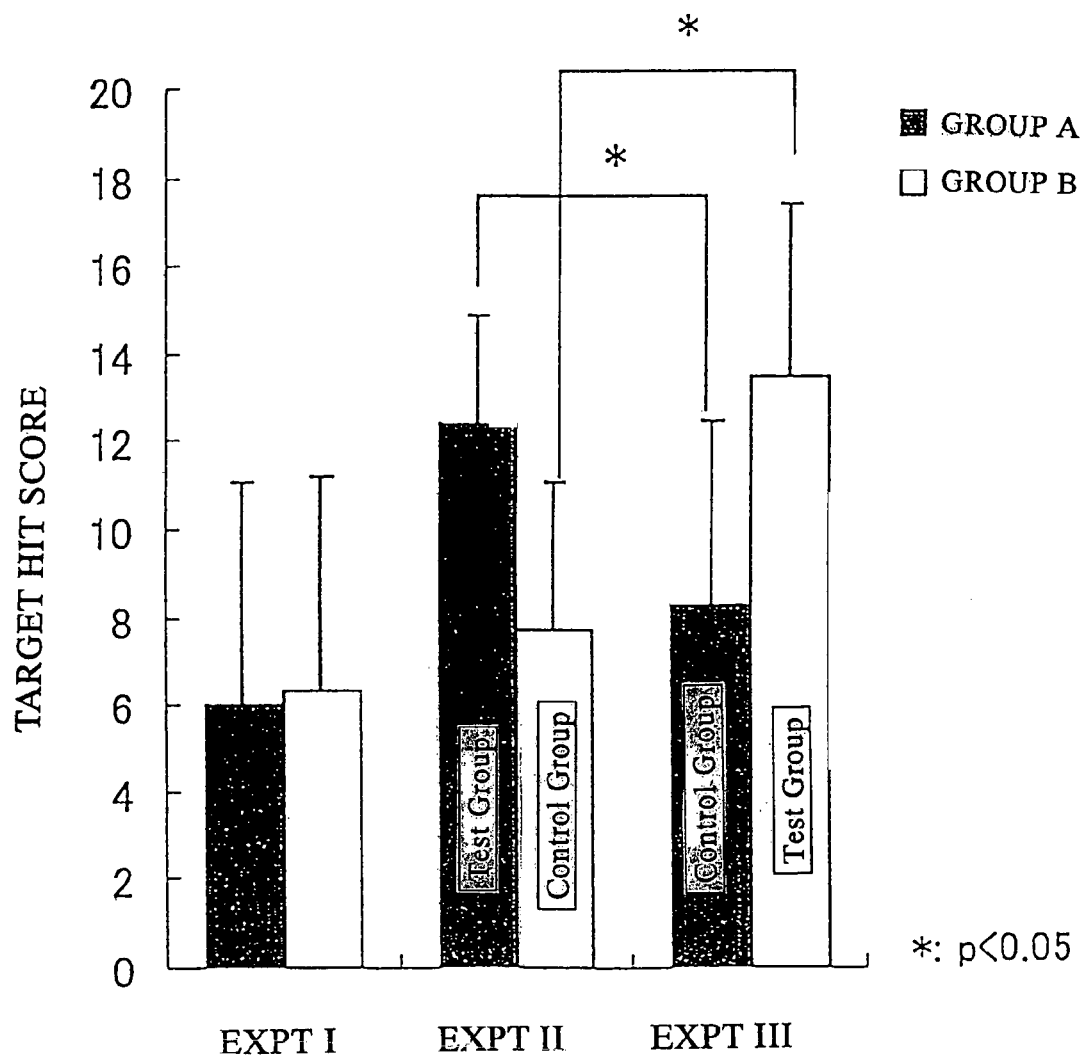
FIG. 7 is a bar chart showing the target hit score (average value) of the subjects (for each group) in the Japanese bow shooting. In the chart, the bar indicates the target hit score, and a line segment drawn perpendicularly from an upper end of the bar shows standard deviation (S.D.). The statistic processing was conducted by Student paired t-test.
Figure 8:
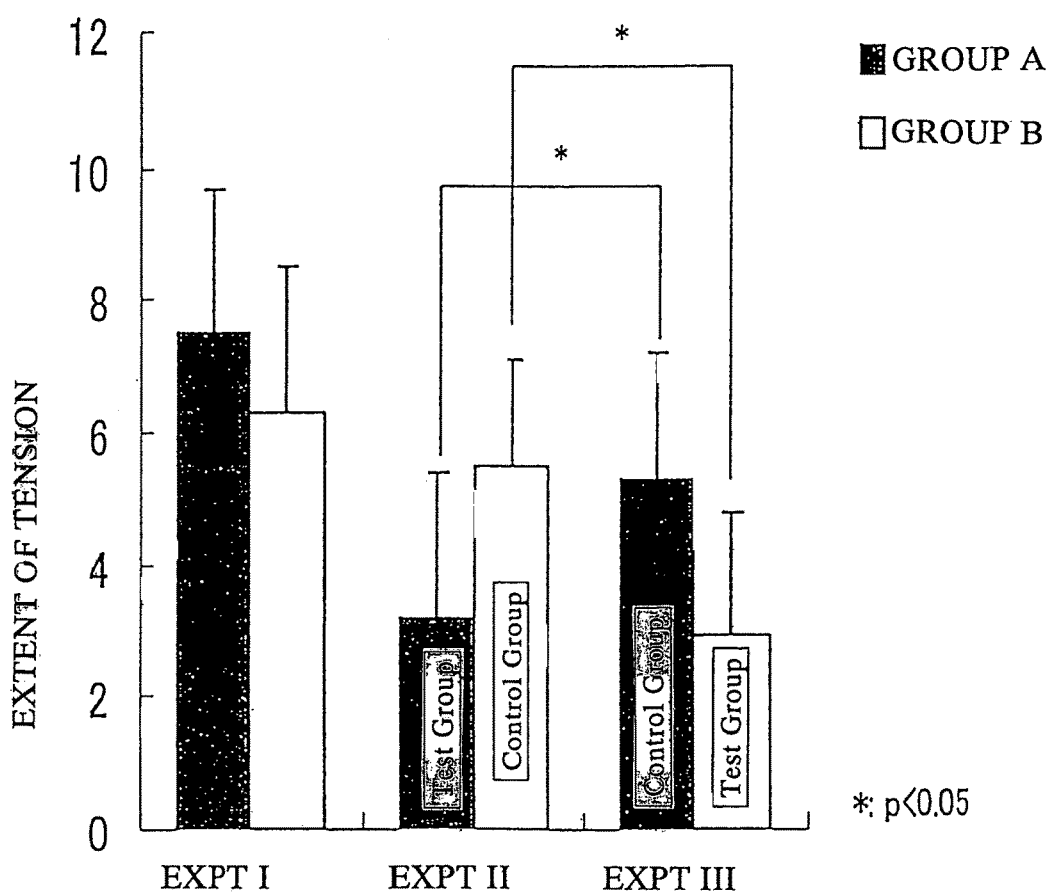
FIG. 8 is a bar chart showing the extent of tension (average value) of the subjects (for each group) according to the questionnaire survey in Japanese bow shooting. In the chart, the bar indicates the extent of tension, and a line segment drawn perpendicularly from an upper end of the bar shows standard deviation (S.D.). The statistic processing was conducted by Student paired t-test.
Figure 9:
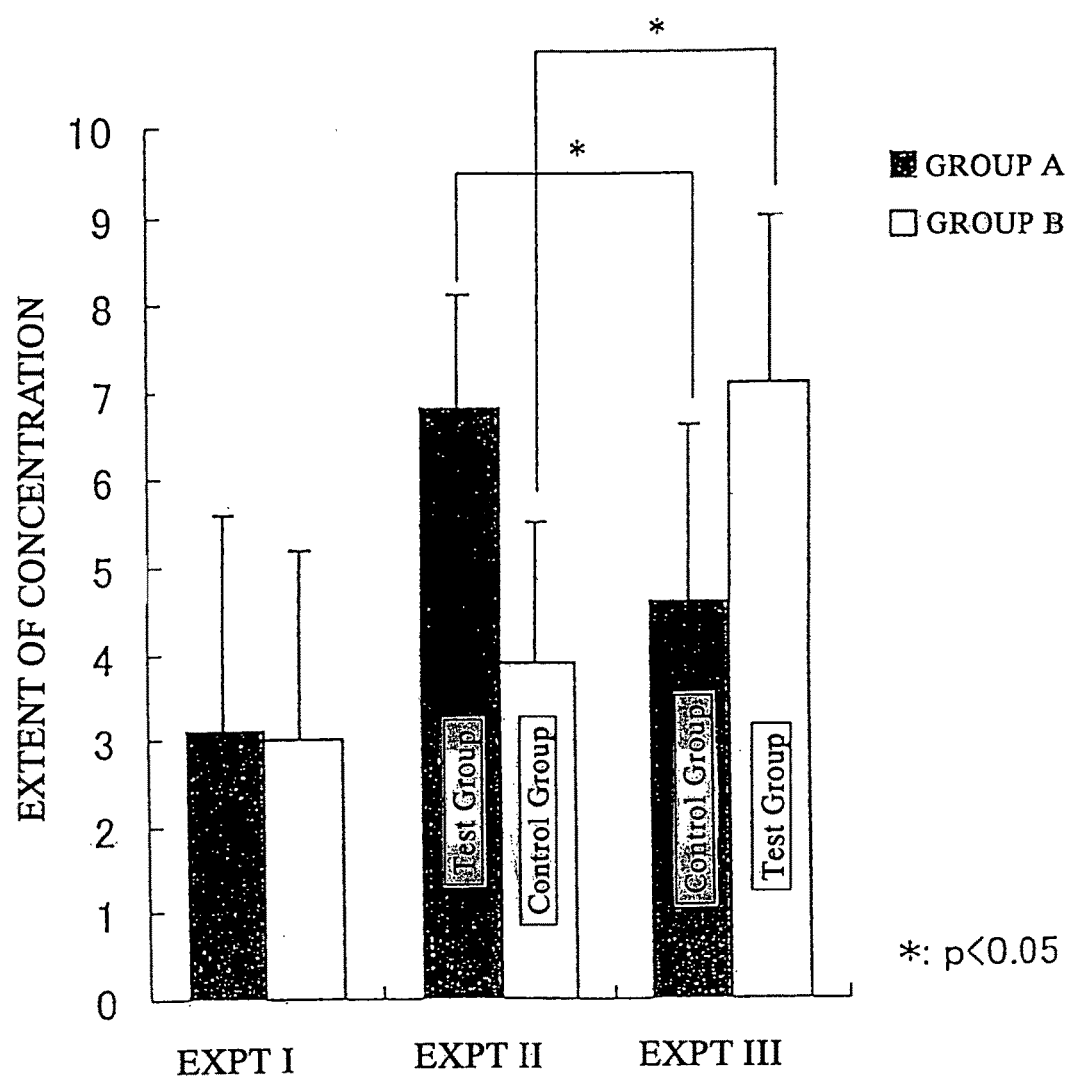
FIG. 9 is a bar chart showing the extent of concentration (average value) of the subjects (for each group) according to the questionnaire survey in the Japanese bow shooting. In the chart, the bar indicates the extent of concentration, and a line segment drawn perpendicularly from an upper end of the bar shows standard deviation (S.D.). The statistic processing was conducted by Student paired t-test.

(2) Main Test
 i) Method
Subsequently, a main test was conducted. First, each subject performed bow shooting at a shooting hall on six consecutive days (Monday through Saturday). The subjects were divided into 10 teams of three shooters on the bases of the target hit scores of each subject, so that the average score in each team was almost the same level among the teams (Experiment I). Next week, 5 out of the 10 teams (Group A), the test group, were allowed to take three theanine-formulated chewable tablets (amount of L-theanine: 600 mg) prepared in Example 5, and the remaining 5 teams (Group B), the control group, were allowed to take three control chewable tablets prepared in Comparative Example 2, each subject taking all three tablets as test substances within 5 minutes at a point of 30 minutes before shooting. Bow shootings were performed at the shooting hall on six consecutive days, and the scores were recorded (Experiment II). Still the next week, the same bow shootings were performed but the test group was exchanged with the control group, and the scores were recorded (Experiment III). For each Experiment, a questionnaire survey was conducted in the same manner as above. Throughout the test period, each subject was not informed of what the test substance was. In the totaling of the target hit scores, the sum of the 6-day scores of each subject was averaged for each group.
 ii) Results
FIG. 7 shows the target hit scores (average values) of the subjects (for each group) in Experiments I, II and III. FIGS. 8 and 9 show the scores of the tension and the concentration recorded according to the questionnaire survey.

It is seen from the comparison of the target hit scores in bow shooting between the test group and the control group that the scores significantly increase in the test group as compared to that of the control group. Also, it is seen from the comparison of the tension and the concentration that the tension significantly decrease in the test group as compared to that of the control group, whereas the concentration significantly increase in the test group as compared to that of the control group.

Test Example 5: Test for Improving Mind-Concentration in Rifle Shooting

The subjects were 20 male university students (average: 20.3 years old, average weight: 61.0 kg) and 8 female university students (average: 19.8 years old, average weight: 48.5 kg), a total of 28 subjects each belonging to a shooting club.

(1) Preliminary Test
 i) Method
Each subject made three trial shots and three scoring shots in a standing position using an air rifle (4.5 mm, 177-caliber) according to the experimental procedures shown in FIG. 10, and the scores were recorded by a recorder. No. 9 target was used and the distance from the shooting position to the target was 10 meters as in official competitions. After completion of all series of shots, a questionnaire survey was conducted for each series of shots on the subjective concentration on a 10-rank scale from 0 point for "could not concentrate at all" to 10 points for "could concentrate very much", or on the subjective tension on another 10-rank scale from 0 point for "not tense at all" to 10 points for "very tense."

ii) Results

Although some differences were found in scores among the subjects, reflecting the differences in their skills, there were no especially significant differences in the tension and the concentration. Thus, the tension and the concentration were found to be at the same level among the subjects, nonetheless there were some differences in their skills. Therefore, the 28 subjects were divided into two groups (groups A and B) on the bases of their average scores for 3 scoring shots, so that the average score in each group was almost the same level among the groups.

(2) Main Test i) Method

In a main test, each subject made 10 consecutive shots within 15 minutes as in a standing air rifle shooting competition at a shooting hall. After completion of all series of shots, a questionnaire survey was conducted for each series of shots on the subjective concentration on a 10-rank scale from 0 point for "could not concentrate at all" to 10 points for "could concentrate very much", or the subjective tension on another 10-rank scale from 0 point for "not tense at all" to 10 points for "very tense".

Group A, the test group, was allowed to take three theanine-formulated chewable tablets (amount of L-theanine: 600 mg) prepared in Example 5, and Group B, the control group, was allowed to take three control chewable tablets prepared in Comparative Example 2, each subject taking all three tablets as test substances within 5 minutes at a point of 45 minutes before air rifle shooting in a standing position. This standing air rifle shooting was performed at the shooting hall on 3 consecutive days (Tuesday through Thursday), and the scores were recorded (Experiment I). Next week, the same standing air rifle shooting was performed but the test group was exchanged with the control group, and the scores were recorded (Experiment II). In each Experiment, a questionnaire survey was conducted in the same manner as above. Throughout the test period, each subject was not informed of what the test substance was. In the totaling of scores, the scores for the 3 days for each subject were averaged for each group.

ii) Results

Figure 11:
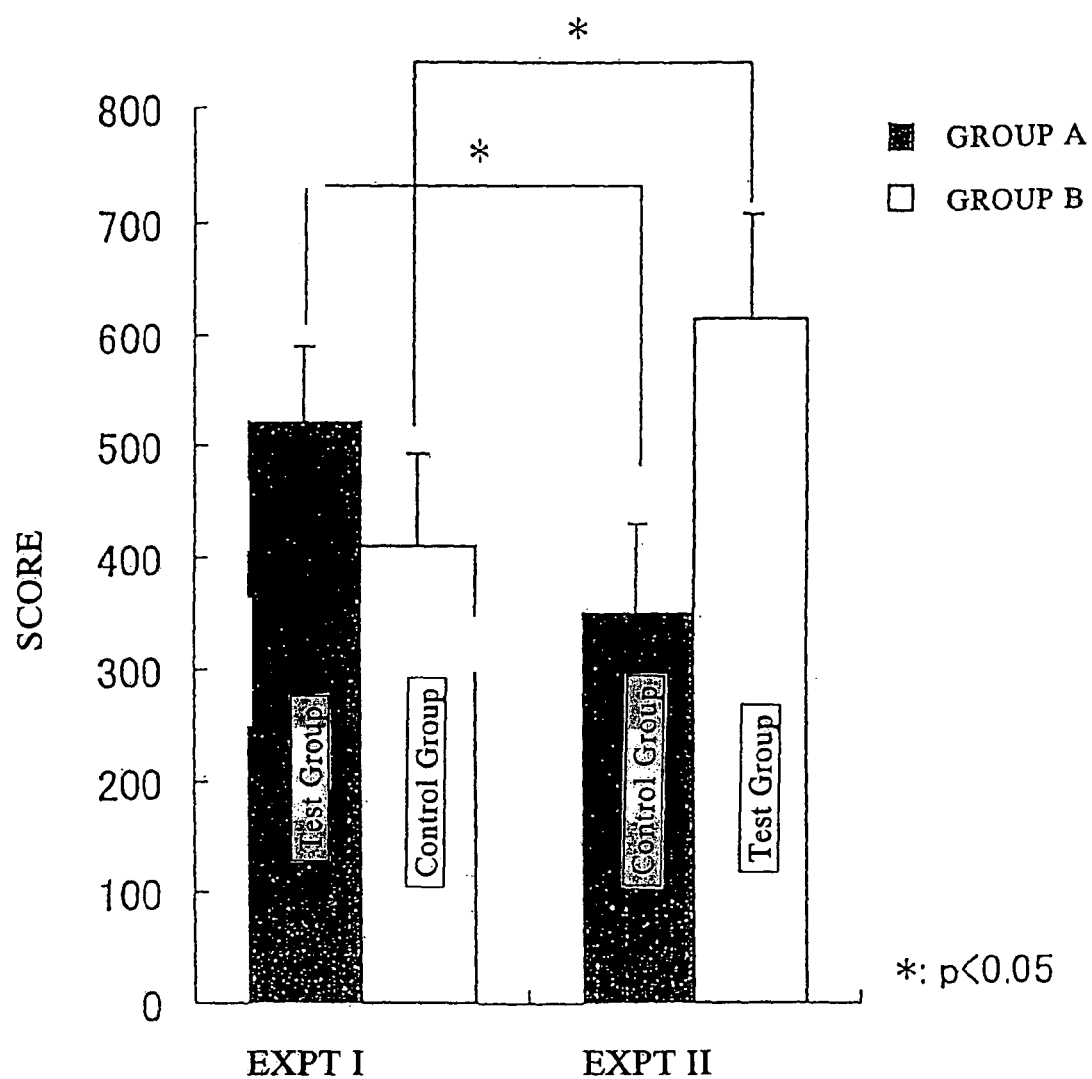
FIG. 11 is a bar chart showing score (average value) of the subjects (for each group) in the air rifle shooting. In the chart, the bar indicates the score, and a line segment drawn perpendicularly from an upper end of the bar shows standard deviation (S.D.). The statistic processing was conducted by Student paired t-test.
Figure 12:
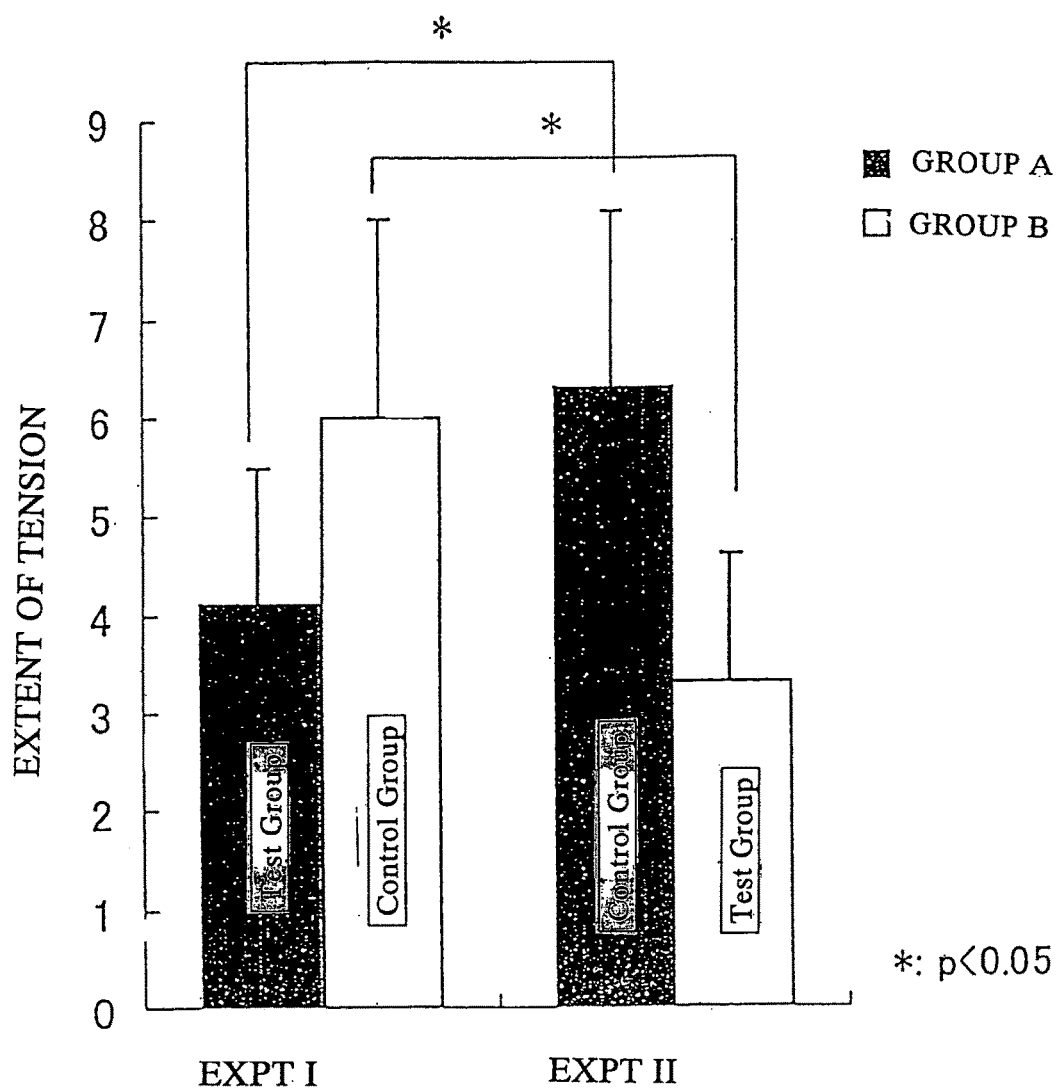
FIG. 12 is a bar chart showing the extent of tension (average value) of the subjects (for each group) according to the questionnaire survey in the air rifle shooting. In the chart, the bar indicates the extent of tension, and a line segment drawn perpendicularly from an upper end of the bar shows standard deviation (S.D.). The statistic processing was conducted by Student paired t-test.
Figure 13:
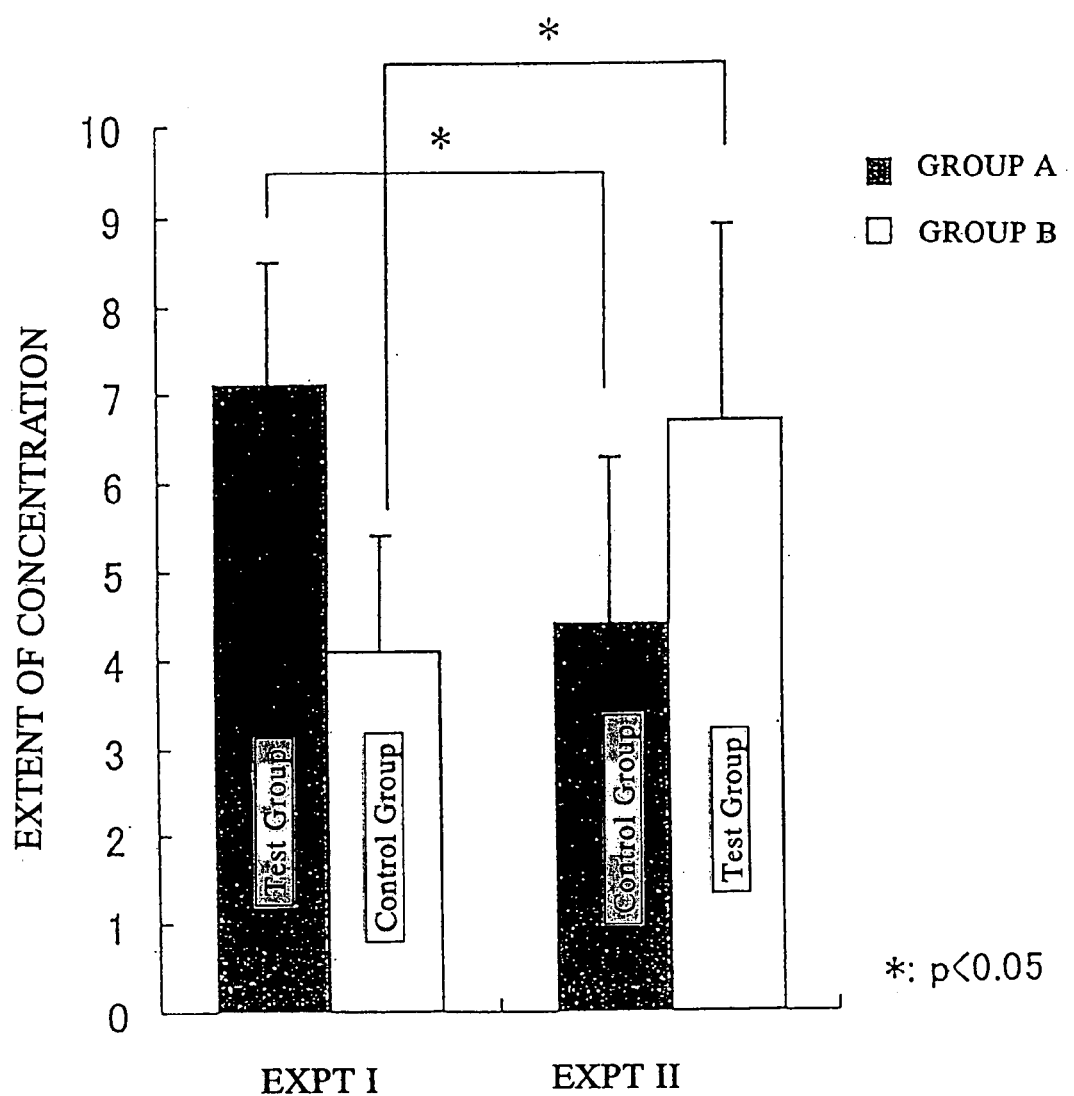
FIG. 13 is a bar chart showing the extent of concentration (average value) of the subjects (for each group) according to the questionnaire survey in the air rifle shooting. In the chart, the bar indicates the extent of concentration, and a line segment drawn perpendicularly from an upper end of the bar shows standard deviation (S.D.). The statistic processing was conducted by Student paired t-test.

FIG. 11 shows the scores (average values) of the subjects (for each group) in Experiments I and II. FIGS. 12 and 13 show the scores of the tension and the concentration recorded according to the questionnaire survey.

It is seen from the comparison of the scores in standing air rifle shooting between the test group and the control group that the scores significantly increase in the test group as compared to that of the control group. Also, it is seen from the comparison on the tension and the concentration that the tension significantly decrease in the test group as compared to that of the control group, whereas the concentration significantly increase in the test group as compared to that of the control group.

Test Example 6: Test for Improving Mind-Concentration in Concentration to One Point for Soccer (Football) Players The subjects were 52 male high school students belonging to a soccer (football) club (average age: 17.3 years old, average weight: 58.3 kg).

(1) Method

The test was conducted using a concentration level meter Model AF (Inaba Tech. Inst.). The record for the concentration to one point was obtained in the same manner as in Test Example 1.

Figure 14:
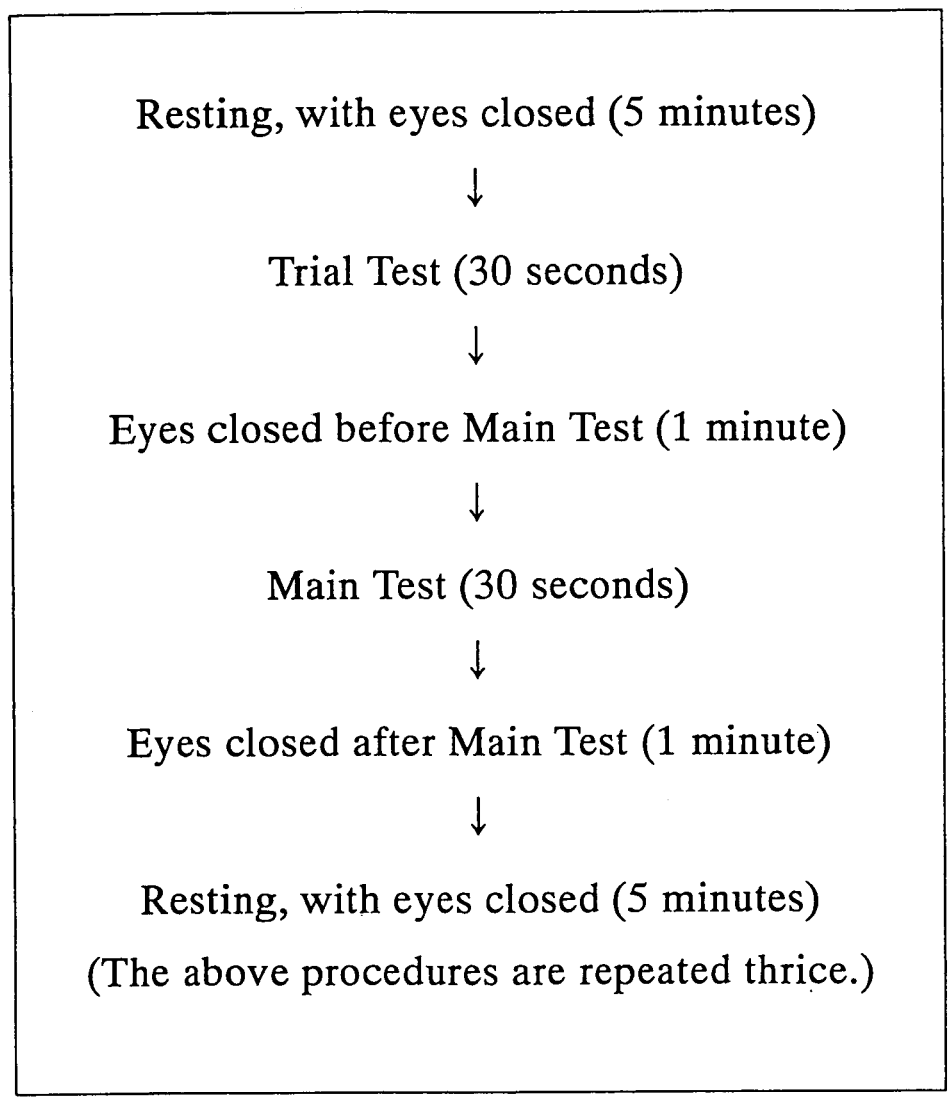
FIG. 14 is a flow chart showing measurement procedures for the record for the one-point concentration using an attentiveness gauge.

First, a preliminary test was conducted, and the subjects were divided into two groups (Groups A and B), so that the records for the concentration to one point as measured by the concentration level meter were almost the same level between the groups. Each subject was asked to sit on a chair in the laboratory, and the record for the concentration to one point was determined according to the procedures shown in FIG. 14. Group A, the test group, was allowed to take one theanine-formulated chewable tablet (amount of L-theanine: 200 mg) prepared in Example 5, and Group B, the control group, was allowed to take one control chewable tablet prepared in Comparative Example 2, each subject taking the tablet as a test substance within 5 minutes at a point of 30 minutes before the determination. This determination was carried out for 3 consecutive days (Experiment I). Next week, the same determination was conducted but the test group was exchanged with the control group (Experiment II). Throughout the test period, each subject was not informed of what the test substance was. In the totaling of results, the records for the concentration to one point (percentage of correct responses) (%) for 3 days of each of the subjects were averaged for each group.

(2) Results

Figure 15:
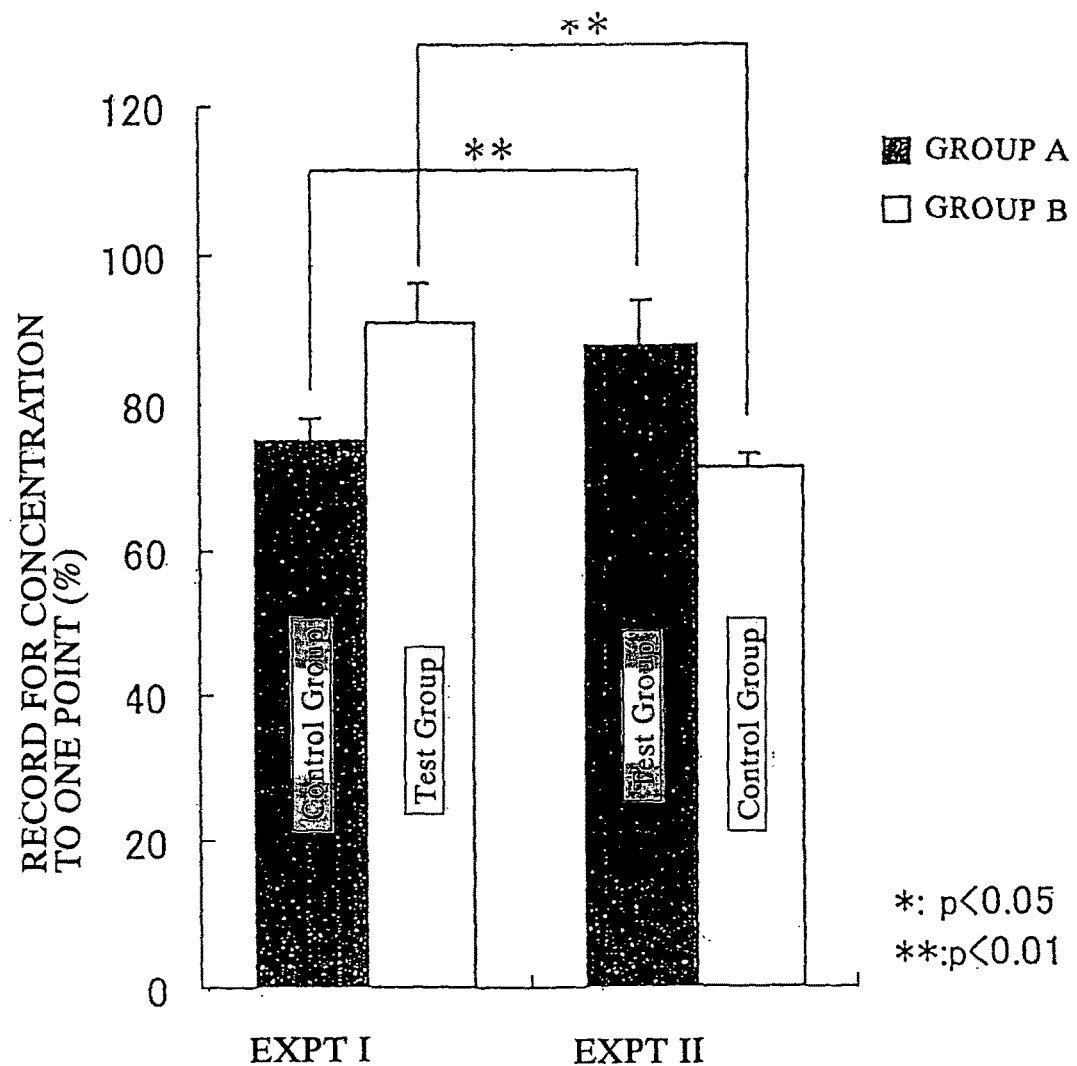
FIG. 15 is a bar chart showing the record for the one-point concentration (average value) of the subjects (for each group) in the one-point concentration. In the chart, each bar shows the record for the one-point concentration, and a line segment drawn perpendicularly from an upper end of the bar shows standard deviation (S.D.). The statistic processing was conducted by Student paired t-test.

FIG. 15 shows the records for the concentration to one point (average values) of the subjects (for each group) in Experiments I and II. It is seen from the comparison between the test group and the control group that the records for the concentration to one point significantly increase in the test group as compared to that of the control group.

Test Example 7: Effects of Theanine on Brain Waves During Long-Period Endurance Physical Exercise The subjects were 15 healthy males (non-smokers) (average age: 27.9 years old, average weight: 83.5 kg) who have been trained for endurance and staying power, or done such training as weight lifting. None of them were taking medication regularly. The content of the test particulars was provided by informed consent. Having confirmed the absence of a cardiovascular disease in a preliminary survey, the subjects were divided into groups (Groups A, B and C) according to their physical exercise abilities, so that the physical exercise ability was almost the same level among the groups. One of the subjects dropped out from the test due to illness, so that the test was finally conducted with 14 participants.

(1) Method

The Preliminary Test was conducted before the Main Test. Both tests were conducted using the same bicycle ergometer (manufactured by Takei Scientific Instruments Co., Ltd.) with the subject in an upright position. In the preliminary test, the test was started at a load of 50 W, and the load was increased by 50 W for every three minutes thereafter, and the subject was asked to pedal the bicycle ergometer until a point where he became thoroughly tired (until a point where the subject could not maintain a given load for 3 minutes, the load being increased in 5 stages). The final load at the point where the subject became thoroughly tired was defined as the maximum tolerable load of the subject, serving as a standard value (the total length of loading time was maximally 16 minutes).

Figure 16:
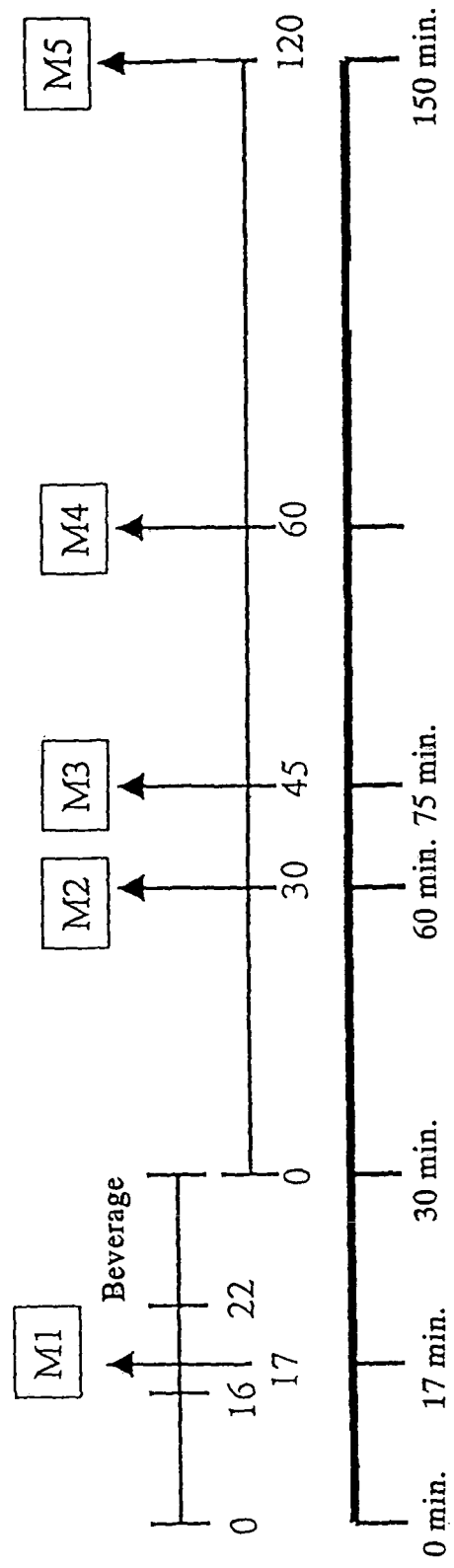
FIG. 16 is a diagram showing the timing of the electroencephalography during a long-period endurance physical exercise in the Main Test. In the diagram, M is the timing of the electroencephalography, and the time scales shown by horizontal lanes indicate a time period (minutes) passed from the beginning of the test shown by a lower lane, and a time period passed shown by an upper lane which consists of a time period passed up to the intake of the test substance and a time period passed after the intake of the test substance, in which pedaling bicycle Ergometer is restarted.

The method used in the determination of brain waves during long-period endurance physical exercise in the main test is shown in FIG. 16. The test was performed at the same hours in the morning (8:00 am, 8:35 am and 10:20 am) of a fixed day of the week for each subject. Group A was allowed to take the control beverage prepared in Comparative Example 3, Group B was allowed to take the beverage containing 50 mg of theanine prepared in Example 7, and Group C was allowed to take the beverage containing 200 mg of theanine prepared in Example 8. The subjects were also asked to regularly take breakfast (395 kcal) 1 hour before the test.

Brain waves were measured during physical exercise loading according to the procedures shown below. Each subject was ask to put on an electrocap for the electroencephalography and pedaled the bicycle ergometer, with the load increased in five steps from 0 W at initiation of pedaling to the maximum tolerable load (standard) obtained in the preliminary test. Specifically, each subject continued pedaling for 3 minutes in each of steps 1 to 4 and 4 minutes in subsequent step 5. The subject then discontinued pedaling, and the subject was asked to lay down to take 3-minute measurement of brain waves, with his eyes closed, before the intake of the test substance (beverage) (M1).

Each beverage was taken between 22 and 30 minutes after the beginning of the test. Thereafter, pedaling was restarted at the maximum tolerable load for each subject, and the brain wave measurements were taken in the same manner at 30 minutes (M2), 45 minutes (M3), 60 minutes (M4) and 120 minutes (M5) after restart of pedaling. The electroencephalograph used was MediSyst (trade name, manufactured by Linden Co.).

(2) Results

Data on the appearances of $\beta1$ wave and $\beta2$ wave in the subjects at time points M1 before the intake of the beverage, M2, M3, M4 and M5 after the intake of the beverage were averaged for each group. The results are shown in FIGS. 17 and 18, respectively.

Figure 17:
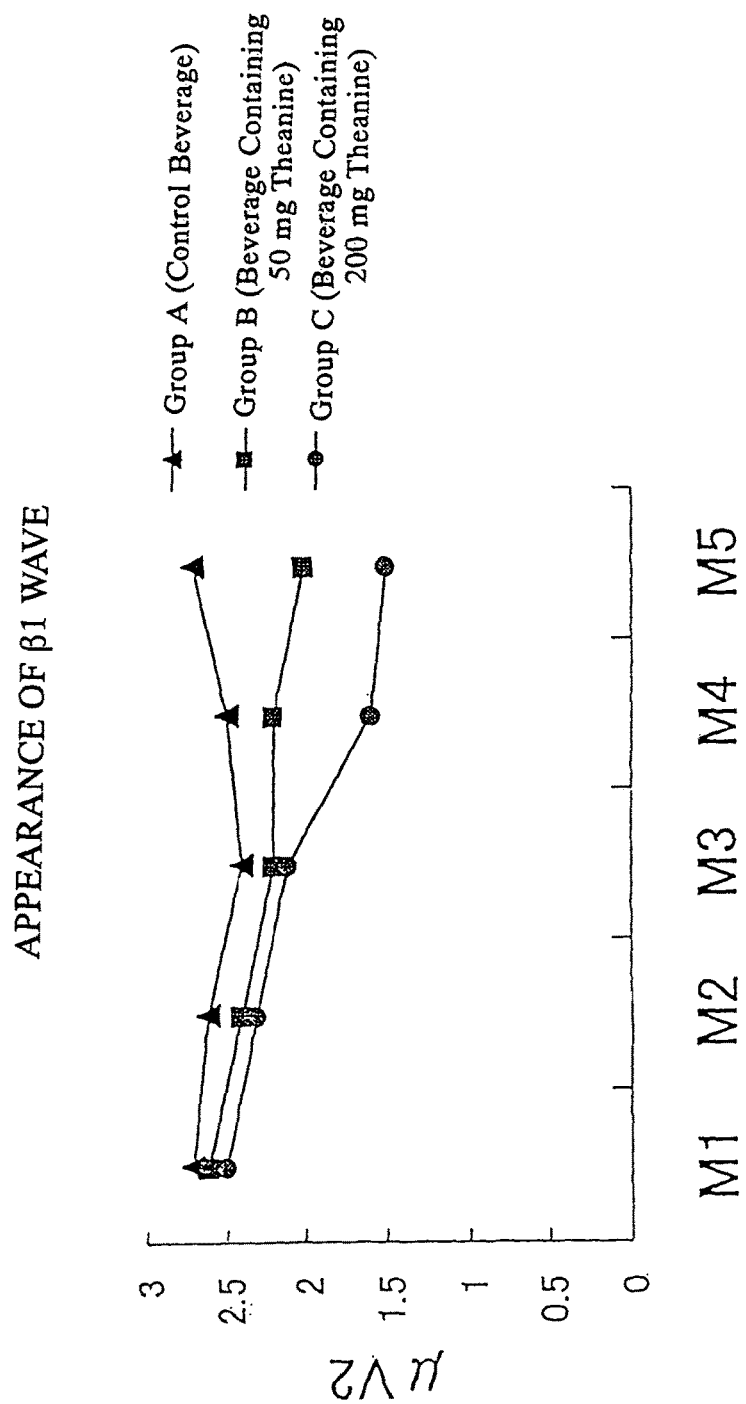
FIG. 17 is a graph showing the appearance of $\beta 1$ wave in the subjects (for each group) during a long-period endurance physical exercise.
Figure 18:
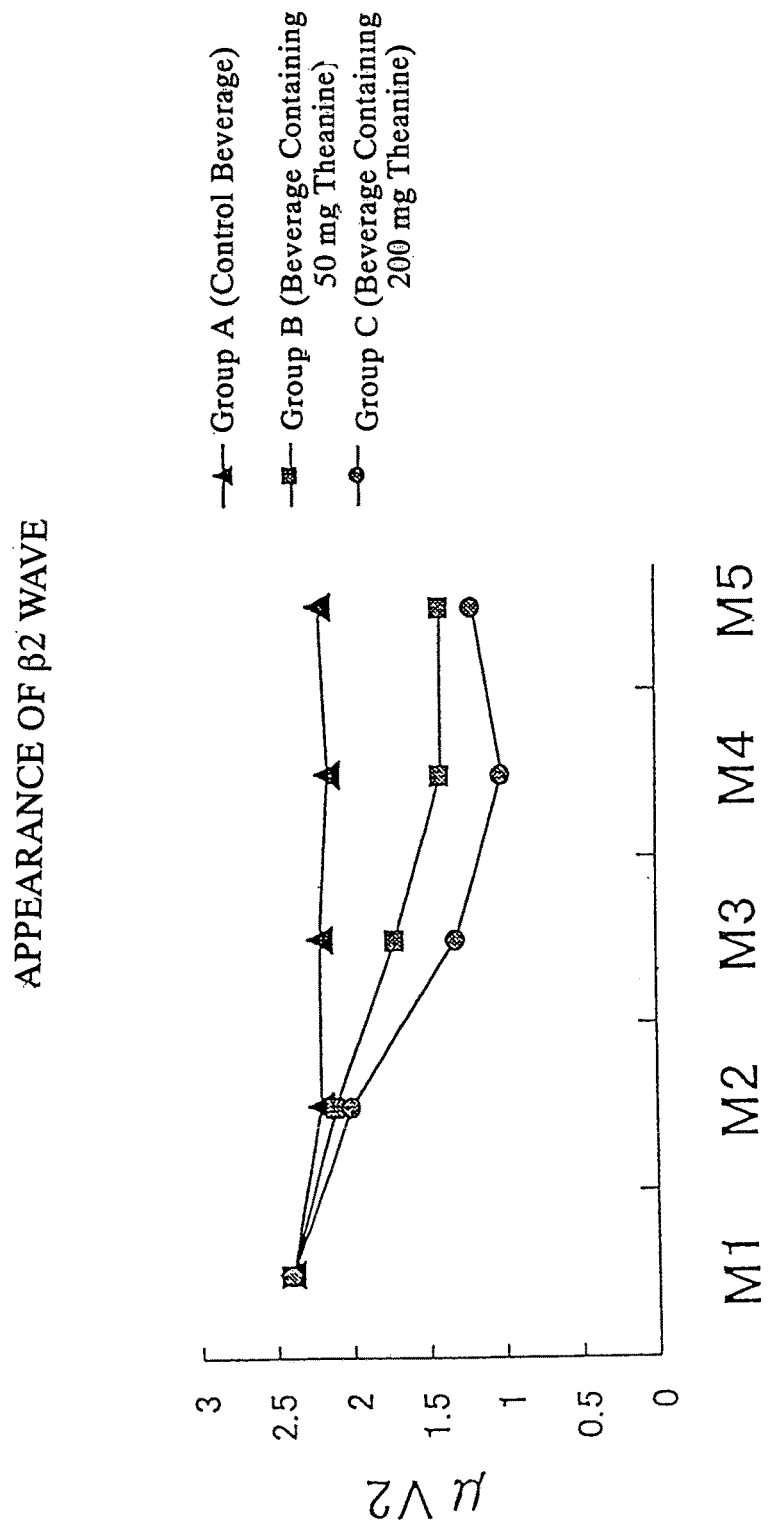
FIG. 18 is a graph showing the appearance of $\beta 2$ wave in the subjects (for each group) during a long-period endurance physical exercise.

It is seen from FIGS. 17 and 18 that the appearance of $\beta$ waves, which are known to appear during irritation, is suppressed in a concentration-dependent manner on theanine by taking a theanine-containing beverage as compared to that of the control beverage containing no theanine. As the endurance physical exercise is continued for a long-period, mental fatigue is accumulated, so that sports performance decreases, wherein the appearance of $\beta$ waves is detected. Since the appearance of $\beta$ waves is suppressed by taking a theanine-containing beverage, it is considered that the psychological effect in the accumulation of the mental fatigue during physical exercise loading is suppressed.

INDUSTRIAL APPLICABILITY

The present invention provides a composition for improving mind-concentration, and a method for improving mind-concentration. According to the present invention, the working efficiency, learning efficiency or the like can be effectively and safely improved, and actual sports performance effectively and safely can be exhibited by (1) suppressing psychological influences and/or physical influences caused by various factors during working, learning or the like, and (2) suppressing psychological influences in psychogenic physical exercise dysfunctions mainly due to tension, shriveling, lowering or lack of concentration, accumulation of mental fatigue or the like during physical exercise, respectively.

The invention claimed is:

1. A method of suppressing generation of $\beta$-waves in brain waves generated during physical exercise, thereby suppressing tension or anxieties in a human individual in sports competitions, comprising the step of:
administering a liquid food comprising theanine to the human individual at a time during physical exercise when $\beta$-waves in brain waves are generated by physical exercise in sports competitions in the human individual;
wherein said composition is in a dose that is from 0.6 to 20 mg theanine/kg individual.

2. The method according to claim 1, wherein said composition is in a dose that is from 9.8 to 20 mg theanine/kg individual.

3. The method according to claim 1, wherein said composition further comprises at least one mineral selected from the group consisting of iron, magnesium, copper, zinc, selenium, calcium, potassium, manganese, chromium, iodine, molybdenum, nickel, vanadium, metal salts thereof, and mixtures thereof.

4. The method according to claim 3, wherein said at least one mineral is present in said composition in an amount of 0.01 to 99.9% by weight.

5. A method of treating a human individual having psychogenic physical exercise dysfunctions, comprising the step of:
suppressing generation of $\beta$-waves in brain waves by administering a liquid food comprising theanine to the human individual during physical exercise in sports competitions;
wherein said composition is in a dose that is from 0.6 to 20 mg theanine/kg individual.

6. A method of treating a human individual having tension or anxieties during physical exercise, comprising the step of:
suppressing generation of $\beta$-waves in brain waves by administering a liquid food comprising theanine to the human individual during physical exercise in sports competitions;
wherein said composition is in a dose that is from 0.6 to 20 mg theanine/kg individual.

7. The method according to claim 5, wherein said composition is in a dose that is from 9.8 to 20 mg theanine/kg individual.

8. The method according to claim 6, wherein said composition is in a dose that is from 9.8 to 20 mg theanine/kg individual.

* * * * *